(12) United States Patent
Page et al.

(10) Patent No.: US 11,534,079 B2
(45) Date of Patent: Dec. 27, 2022

(54) SURGICAL PUNCTURE DEVICE INSERTION SYSTEMS AND RELATED METHODS

(71) Applicant: Intuitive Surgical Operations, Inc., Sunnyvale, CA (US)

(72) Inventors: Brett Myers Page, Santa Clara, CA (US); Simon Peter DiMaio, San Carlos, CA (US); Brandon Itkowitz, San Jose, CA (US); Goran Adrian Lynch, Oakland, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 201 days.

(21) Appl. No.: 16/333,466

(22) PCT Filed: Oct. 11, 2017

(86) PCT No.: PCT/US2017/056189
§ 371 (c)(1),
(2) Date: Mar. 14, 2019

(87) PCT Pub. No.: WO2018/071573
PCT Pub. Date: Apr. 19, 2018

(65) Prior Publication Data
US 2019/0223759 A1 Jul. 25, 2019

Related U.S. Application Data

(60) Provisional application No. 62/407,203, filed on Oct. 12, 2016.

(51) Int. Cl.
*A61B 34/32* (2016.01)
*A61B 17/34* (2006.01)
(Continued)

(52) U.S. Cl.
CPC ............ *A61B 5/065* (2013.01); *A61B 5/6848* (2013.01); *A61B 5/6885* (2013.01);
(Continued)

(58) Field of Classification Search
CPC ......... A61B 34/30; A61B 34/32; A61B 34/35; A61B 34/37; A61B 34/70; A61B 34/71;
(Continued)

(56) References Cited

U.S. PATENT DOCUMENTS 5,328,458 A * 7/1994 Sekino ................ A61M 13/003
604/23
2002/0198554 A1* 12/2002 Whitman ........... A61B 17/3476
606/167

(Continued)

FOREIGN PATENT DOCUMENTS

JP 2006271546 A 10/2006
WO WO-2014002805 A1 1/2014

OTHER PUBLICATIONS

International Search Report and Written Opinion for Application No. PCT/US2017/056189, dated Feb. 7, 2018, 22 pages.
(Continued)

*Primary Examiner* — Kathleen S Holwerda
(74) *Attorney, Agent, or Firm* — Fish & Richardson P.C.

(57) ABSTRACT

A medical puncture device system includes a puncture device, a sensor, and an indicator system. The puncture device is configured to create a puncture through patient tissue and into an internal patient cavity to enable a medical tool to be inserted through the puncture into the cavity. The sensor is configured to generate a signal indicative of motion of the puncture device through the tissue into the cavity. The indicator system is operable by a controller to produce human-perceptible feedback in response to the signal generated by the sensor.

30 Claims, 17 Drawing Sheets

(51) Int. Cl.
| | |
|---|---|
| A61B 5/06 | (2006.01) |
| A61B 5/00 | (2006.01) |
| A61B 34/37 | (2016.01) |
| A61B 34/35 | (2016.01) |
| A61B 34/30 | (2016.01) |
| A61B 5/11 | (2006.01) |
| A61B 17/00 | (2006.01) |
| A61B 90/00 | (2016.01) |

(52) U.S. Cl.
CPC .......... *A61B 17/3421* (2013.01); *A61B 34/30* (2016.02); *A61B 34/32* (2016.02); *A61B 34/35* (2016.02); *A61B 34/37* (2016.02); *A61B 5/11* (2013.01); *A61B 2017/00022* (2013.01); *A61B 2017/00026* (2013.01); *A61B 2017/00039* (2013.01); *A61B 2017/00057* (2013.01); *A61B 2017/00075* (2013.01); *A61B 2017/00106* (2013.01); *A61B 2017/3409* (2013.01); *A61B 2034/302* (2016.02); *A61B 2090/065* (2016.02); *A61B 2090/374* (2016.02); *A61B 2090/376* (2016.02); *A61B 2090/3762* (2016.02)

(58) Field of Classification Search
CPC ......... A61B 34/72; A61B 34/20; A61B 90/11; A61B 17/3403; A61B 17/3421; A61B 2017/00026; A61B 2017/00039; A61B 2017/00057; A61B 2017/00075; A61B 2017/3405; A61B 2017/3407; A61B 2017/3409; A61B 90/50; A61B 90/10; A61B 17/34

See application file for complete search history.

(56) References Cited

U.S. PATENT DOCUMENTS

| | | | | |
|---|---|---|---|---|
| 2003/0097060 | A1* | 5/2003 | Yanof | A61B 34/70 600/424 |
| 2007/0249911 | A1* | 10/2007 | Simon | G16H 70/20 600/300 |
| 2008/0097165 | A1* | 4/2008 | Gattani | A61B 6/12 600/300 |
| 2008/0249467 | A1* | 10/2008 | Burnett | A61B 17/3417 604/117 |
| 2010/0010505 | A1 | 1/2010 | Herlihy et al. | |
| 2010/0274191 | A1* | 10/2010 | Ting | A61B 17/3403 604/116 |
| 2010/0274202 | A1 | 10/2010 | Hyde et al. | |
| 2011/0071473 | A1 | 3/2011 | Rogers et al. | |
| 2011/0071543 | A1 | 3/2011 | Prisco et al. | |
| 2012/0158011 | A1* | 6/2012 | Sandhu | A61B 34/30 606/130 |
| 2016/0008075 | A1* | 1/2016 | Velhamos | A61B 17/3474 600/464 |
| 2016/0008082 | A1* | 1/2016 | Takagi | A61B 17/3403 606/130 |
| 2016/0128781 | A1* | 5/2016 | Blohm | A61B 34/30 606/130 |

OTHER PUBLICATIONS

A Novel Device for Peritoneal Access in Laparoscopic Surgery, Jul. 7, 2011, 5 pages, [online], [retrieved on Oct. 7, 2016], Retrieved from the Internet: http://www.obgyn.net/laparoscopy/novel-device-peritoneal-access-laparoscopic-surgery.

Mayol J., et al.,"Risks of the Minimal Access Approach for Laparoscopic Surgery: Multivariate Analysis of Morbidity Related to Umbilical Trocar Insertion," World Journal of Surgery, Jun. 1997, vol. 21(5), pp. 529-533.

Taye M.K., et al., "Open Versus Closed Laparoscopy: Yet an Unresolved Controversy," Journal of Clinical and Diagnostic Research, Feb. 2016, vol. 10(2), pp. QC04-QC07. DOI: 10.7860/JCDR/2016/18049.7252.

Vilos G.A., et al., "Laparoscopic Entry: A Review of Techniques, Technologies, and Complications," Journal of Obstetrics and Gynaecology Canada, SOGC Clinical Practice Guideline, May 1997, vol. 193, pp. 443-447.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL PUNCTURE DEVICE INSERTION SYSTEMS AND RELATED METHODS

CROSS REFERENCE TO RELATED APPLICATIONS

This application is a U.S. National Stage Application under 35 U.S.C. § 371 and claims the benefit of International Patent Application No. PCT/US2017/056189, filed on Oct. 11, 2017 which claims the benefit of U.S. Provisional Application No. 62/407,203, filed Oct. 12, 2016. The disclosures of the prior applications are considered part of and are incorporated by reference in the disclosure of this application.

TECHNICAL FIELD

This specification relates to medical puncture device insertion systems and methods.

BACKGROUND

Endoscopy is a form of minimally invasive surgery. Laparoscopy is a form of endoscopy involving minimally invasive inspection and surgery inside the abdominal cavity. In a typical laparoscopic surgery, an incision is made such that a surgical instrument can access the abdominal cavity. The patient's abdominal cavity is insufflated with gas, and a sleeve is passed through the incision, e.g., through the patient's body to provide a port to the cavity. The surgical tool is passed through the port into the internal patient cavity and is manipulated to perform a surgical operation on a patient. In a telesurgery system, an operator, e.g., a surgeon, remotely controls manipulation of the surgical tool by manipulating control devices at a location remote from the patient.

SUMMARY

In one aspect, a medical puncture device system includes a puncture device, a sensor, and an indicator system. The puncture device is configured to create a puncture through patient tissue and into an internal patient cavity to enable a medical tool to be inserted into the cavity. The sensor is configured to generate a signal indicative of motion of the puncture device through the tissue into the cavity. The indicator system is operable by a controller to produce human-perceptible feedback in response to the signal generated by the sensor.

In another aspect, a puncture device insertion system includes a remotely controllable manipulator to support a puncture device and to create a puncture through patient tissue into an internal patient cavity, thereby enabling a medical tool to be inserted through the puncture into the cavity. The puncture device insertion system also includes a drive system connected to a joint of the manipulator and operable to control movement of the puncture device. The puncture device insertion system further includes a sensor coupled to the manipulator and configured to generate a signal indicative of motion of the puncture device through the tissue into the cavity. The puncture device insertion system also includes a controller operably coupled to the sensor and the drive system. The controller is configured to operate the drive system, based on the signal, to guide creation of the puncture by the puncture device through the tissue and into the cavity.

In yet another aspect, a method of aiding in insertion of a puncture device includes detecting motion of a puncture device through patient tissue into an internal patient cavity to create a puncture through the tissue into the cavity. The method also includes producing human-perceptible feedback in response to detecting motion of the puncture device through the tissue into the cavity thereby signaling that the cavity is accessible by a medical tool through the puncture.

Advantages of the foregoing may include, but are not limited to, those described below and herein elsewhere. Machine-provided operator feedback during insertion of the puncture device can enable an operator to focus attention on inserting the puncture device to create a puncture through the patient tissue and to enable the medical tool to access the patient cavity. The operator feedback can improve the ease and safety of the puncture, compared with conventional methods in which the operator creates a puncture without such feedback, or pausing at points during the process of creating the puncture to perform manual tests to evaluate the puncture.

In some implementations, rather intuiting a location of the puncture device relative to patient tissue during the insertion based on tactile feelings, the operator can leverage sensor data to more accurately gauge the location of the puncture device. As the puncture device is inserted through the tissue, the feedback can inform the operator of progress of the insertion process and indicate whether the operator should make any adjustments to the manipulation of the puncture device. By guiding the insertion process, the systems and methods described herein can expedite the process of performing a medical operation. In some cases, these systems and methods can reduce operator error. The human-perceptible feedback can further prevent the operator from moving the puncture device in a manner that can increase the likelihood of complications during the process of creating the puncture with the puncture device.

In some implementations, the sensor data is used for autonomous control of the puncture device to reduce the risk of human error. The puncture device is guided autonomously through control of a drive system, e.g., of a manipulator, and the sensor data can be used to ensure that the puncture device in a safe manner through patient tissue.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
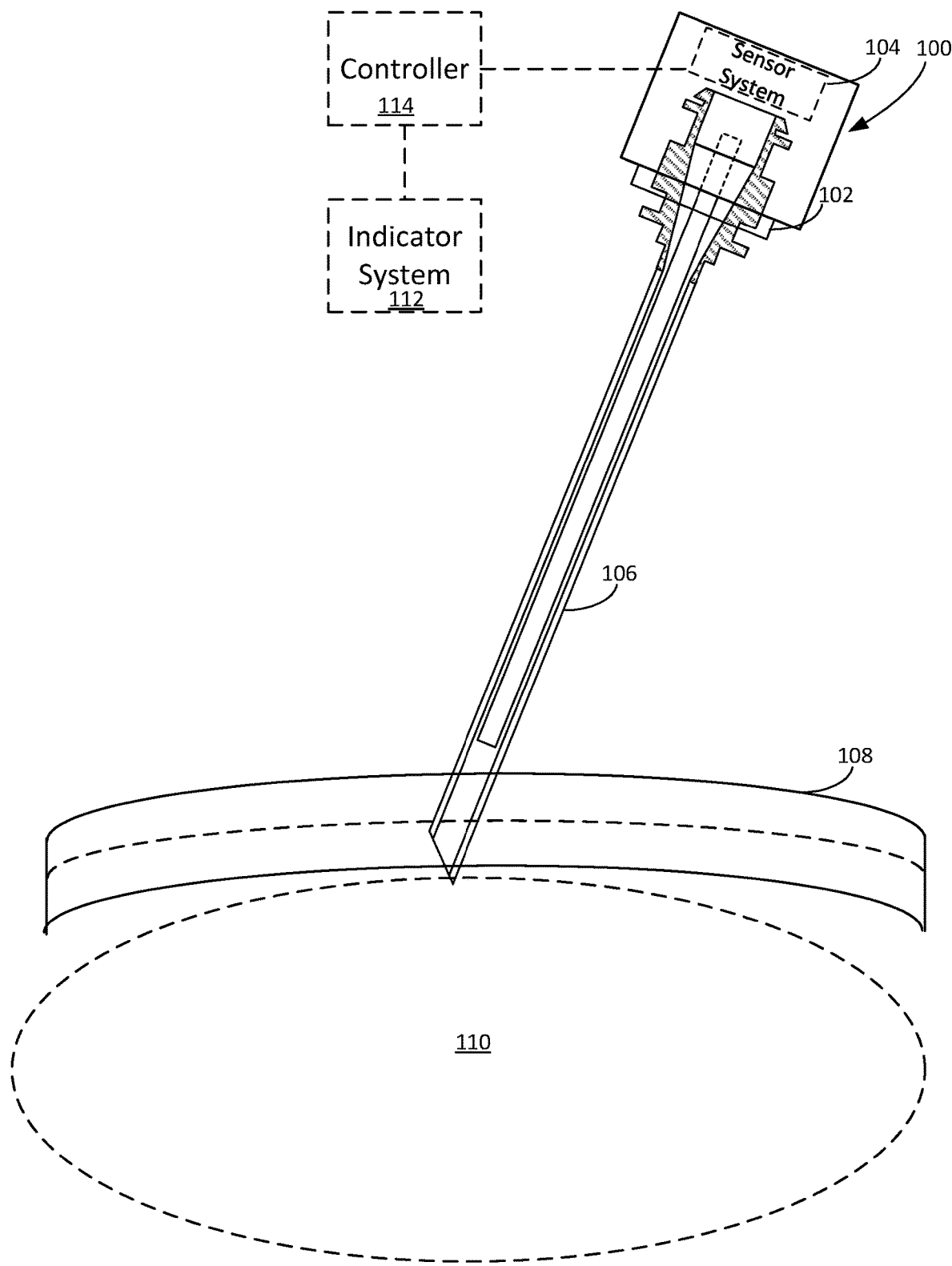
FIG. 1 is a side view of a surgical puncture device insertion system including a puncture device inserted through tissue of a patient.

A puncture device can be used to create a puncture through patient tissue and into an internal patient cavity to enable a medical tool, e.g., a surgical tool, to access the internal patient cavity. In particular, the medical tool can be inserted through the puncture such that the medical tool can be used to perform a medical operation. In some implementations, a puncture device with a port, such as a cannula, can be positioned to extend through the puncture. The medical tool can be inserted through the port to perform the medical operation within the internal patient cavity. The puncture device can be manually manipulated by a human operator, e.g., a surgeon, and be moved through the patient tissue and into the internal patient cavity to form the puncture. The systems, devices, and methods described herein can enable monitoring of the insertion of the puncture device, e.g., using sensors, such that parameters relevant to the insertion are maintained within predefined ranges. In addition, these systems, devices, and methods can provide guidance, e.g., by providing human-perceptible feedback to the human operator, by controlling motion of the puncture device, etc., such that the puncture can be quickly created without increasing the risk of causing complications to the patient.
Example Medical Puncture Device Insertion Systems and Related Methods FIG. 1 shows an example of a medical puncture device insertion system usable for a surgical operation. In the example shown in FIG. 1, a surgical puncture device insertion system 100 includes a puncture device holder 102 and a sensor system 104. The puncture device holder 102 supports a puncture device 106 to be used to create a puncture on a body wall of a patient. The puncture, for instance, extends through tissue 108 of the patient and into an internal patient cavity 110. The puncture created by the puncture device 106 enables a surgical tool to be inserted into the cavity 110 through the puncture. The puncture created by the puncture device 106 enables a surgical tool to be inserted into the cavity 110 through that first puncture, or a second puncture made after insufflation is achieved using that first puncture. Example surgical tools include sensing and imaging devices such as endoscopes and cameras, and medical instruments for cutting, cauterizing, suturing, grasping, stapling, or otherwise interacting with tissue.

The sensor system 104 includes, for example, a sensor that generates signals in response to motion of the puncture device 106. As the puncture device 106 is inserted through the tissue 108, the sensor system 104 generates a signal indicative of motion of the puncture device 106 through the tissue into the cavity 110. In some implementations, the sensor system 104 is physically coupled to the puncture device holder 102.

Many variations to the insertion system 100 are possible. For example, some implementations may not include a puncture device holder 102, and the sensor system 104 may be physically separate from the puncture device 106 in whole or in part.

Figure 2:
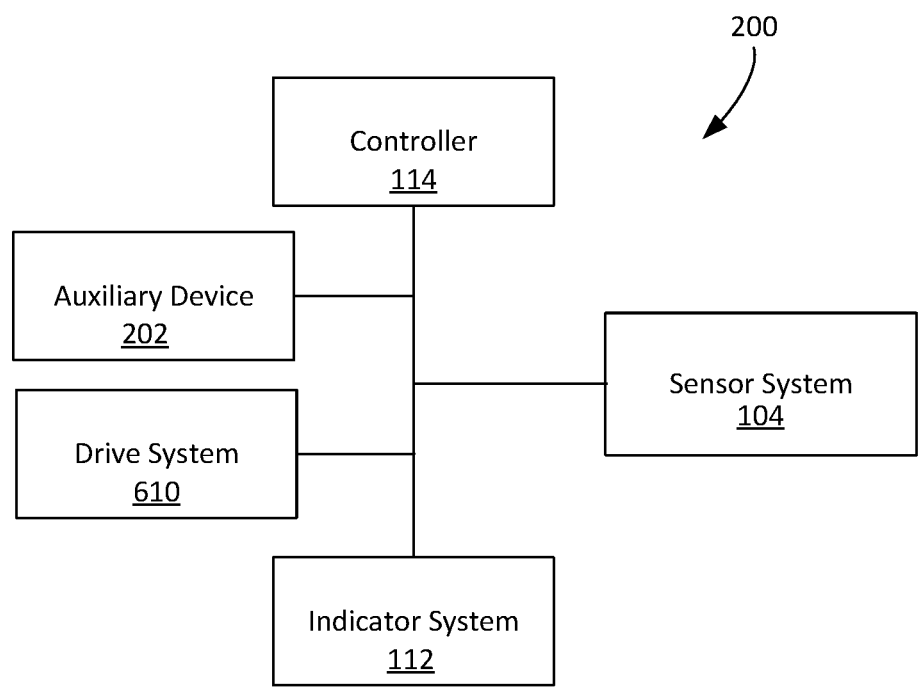
FIG. 2 is a block diagram of a surgical puncture device insertion system.

Referring to the example block diagram 200 shown in FIG. 2, in implementations in which human-perceptible feedback is used to guide creation of the puncture by the puncture device 106, an indicator system 112 is operable by a controller 114 to produce the human-perceptible feedback in response to the signal generated by the sensor system 104. The block diagram 200 may be used with the surgical puncture device insertion system 100. The indicator system 112, in this regard, is operable by the controller 114 to guide motion of the puncture device 106 to form the puncture, e.g., a first access port to provide surgical tool access to the cavity 110. As described herein, rather than or in addition to generating human-perceptible feedback to guide the creation of the puncture, a controller can autonomously control movement of the puncture device 106 to guide the creation of the puncture.

Figure 16:
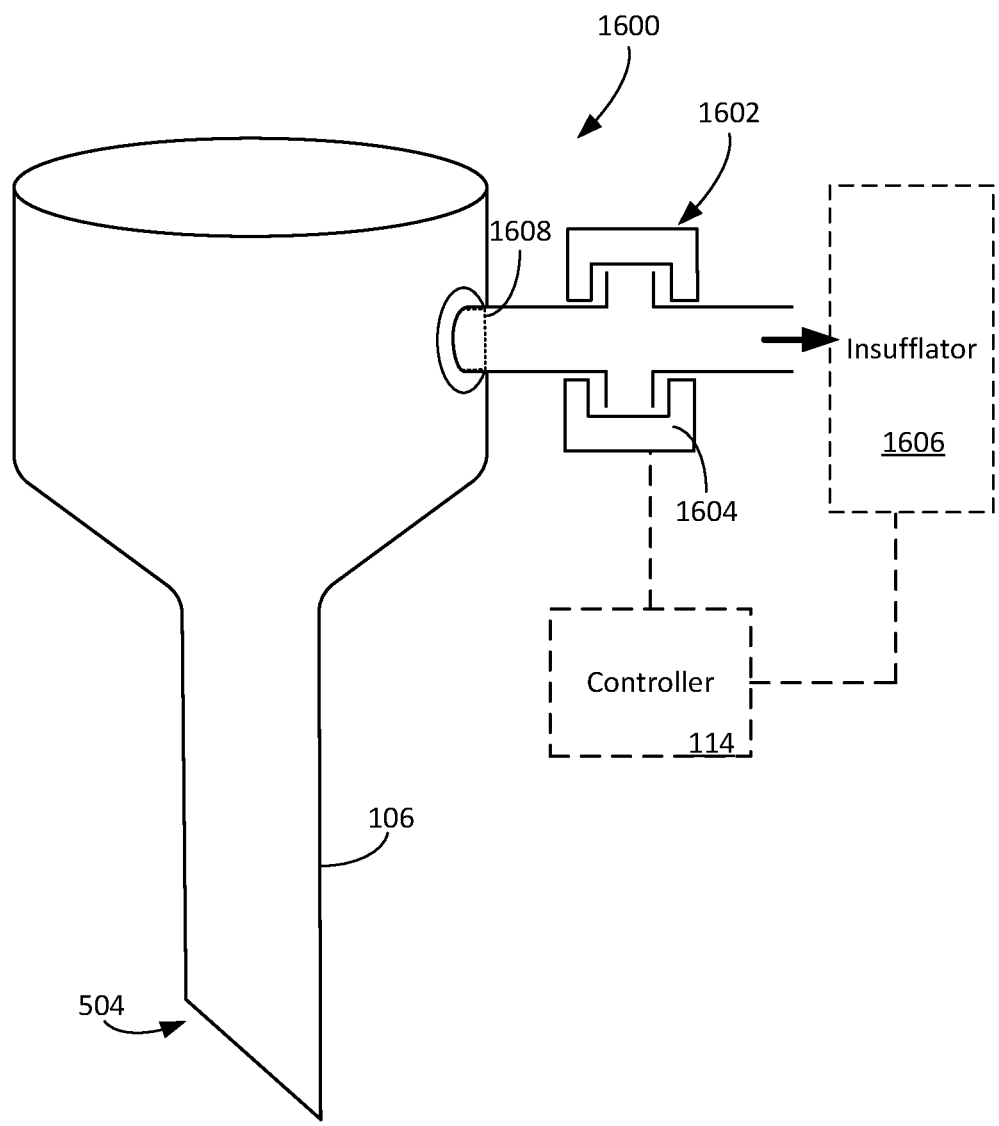
FIG. 16 is a side view of a surgical puncture device insertion system including a pressure sensor.
Figure 17:
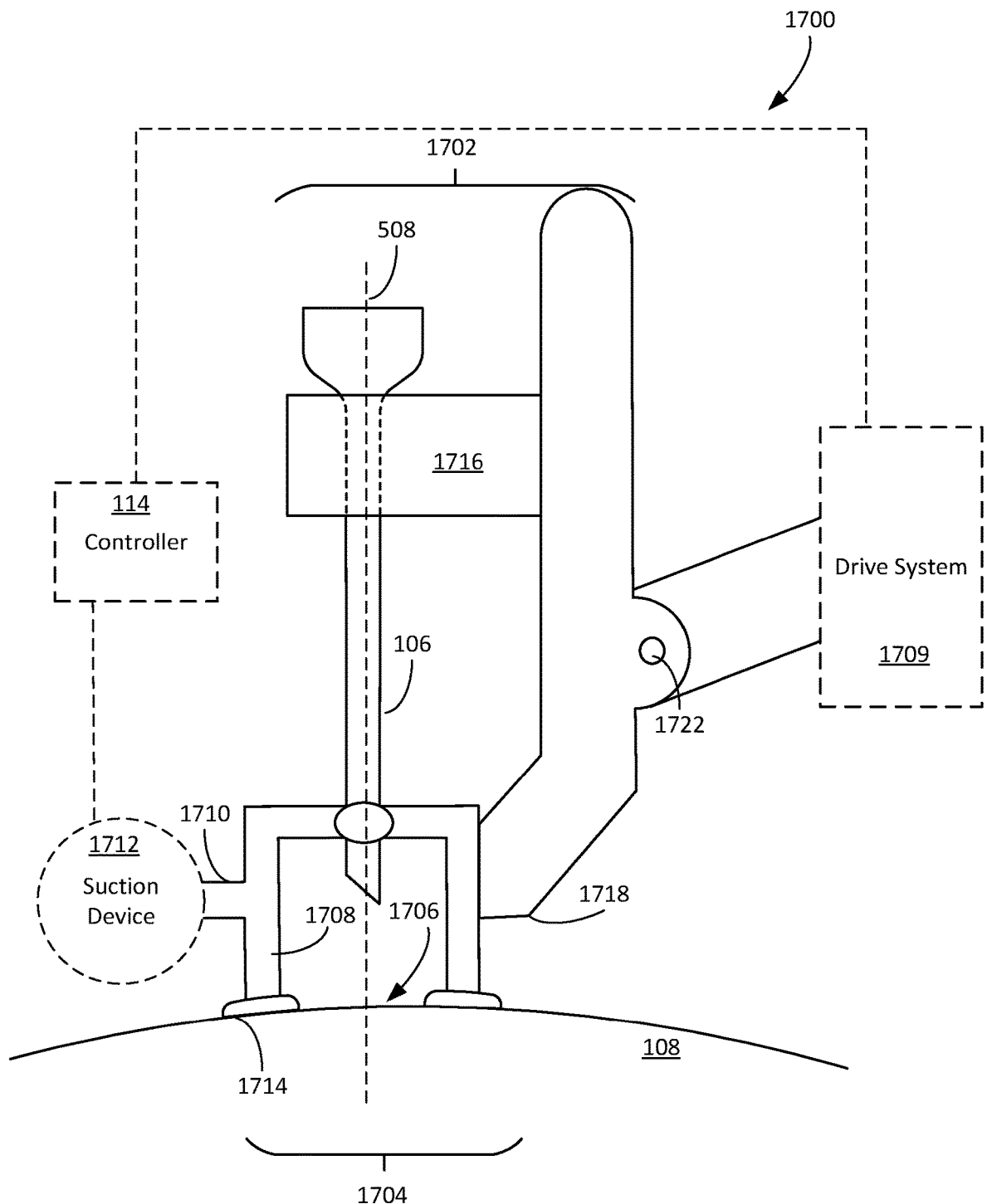
FIG. 17 is a side view of a surgical puncture device insertion system including a stabilizing device.

In some examples, the block diagram 200 further includes an auxiliary device 202. The auxiliary device 202 is, for example, an insufflator, a stabilizing device, other auxiliary device described herein, or any other appropriate auxiliary device. The controller 114 controls operations of the auxiliary device 202, for instance, to support coordination of operations of the sensor system 104. In some cases, as described with respect to FIG. 16, the auxiliary device 202 is an insufflator. In some cases, as described with respect to FIG. 17, the auxiliary device 202 is a stabilizing device to stabilize tissue in a region of an insertion site of the puncture device 106.

Figure 3:
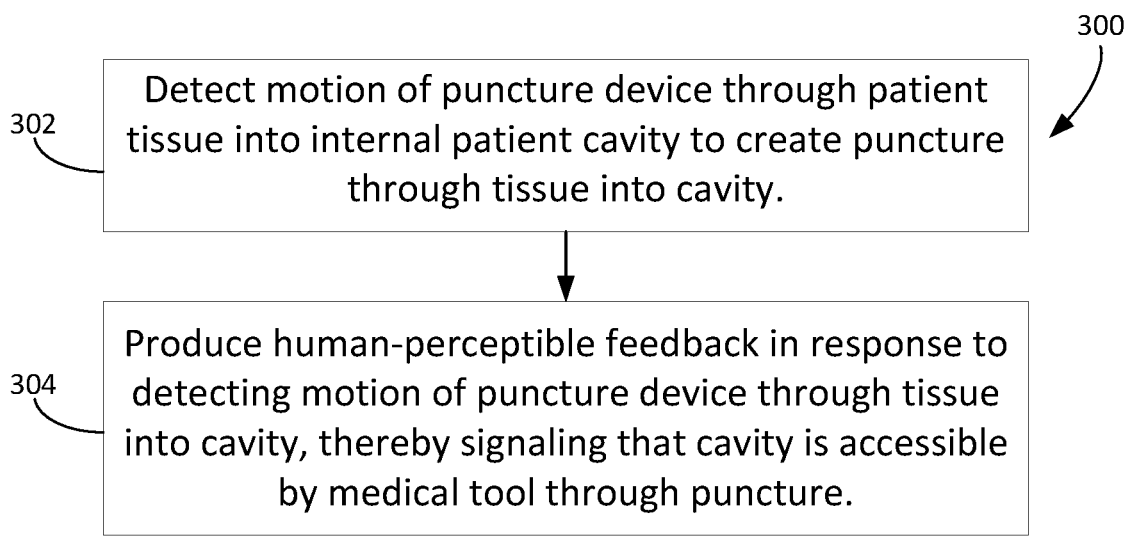
FIG. 3 is a flow chart of a process to guide insertion of a puncture device.

The example flow chart of FIG. 3 depicts a process 300 of aiding in insertion of a puncture device, e.g., the puncture device 106 of FIG. 1. The process 300 is, for example, executed by the controller 114. At an operation 302, the controller 114 detects motion of the puncture device through the tissue 108 into the internal patient cavity 110. At an operation 304, the controller 114 produces human-perceptible feedback in response to detecting motion of the puncture device 106 through the tissue 108 into the cavity 110 to create the puncture through the tissue 108 into the cavity 110. The human-perceptible feedback signifies that the cavity 110 is accessible by the surgical tool, such as through the puncture, an enlargement of the puncture, or a second puncture to be made in the patient tissue after this initial puncture. The controller 114 operates, for example, the indicator system 112 to produce the human-perceptible feedback in response to the signal generated by the sensor system 104.

Figure 4:
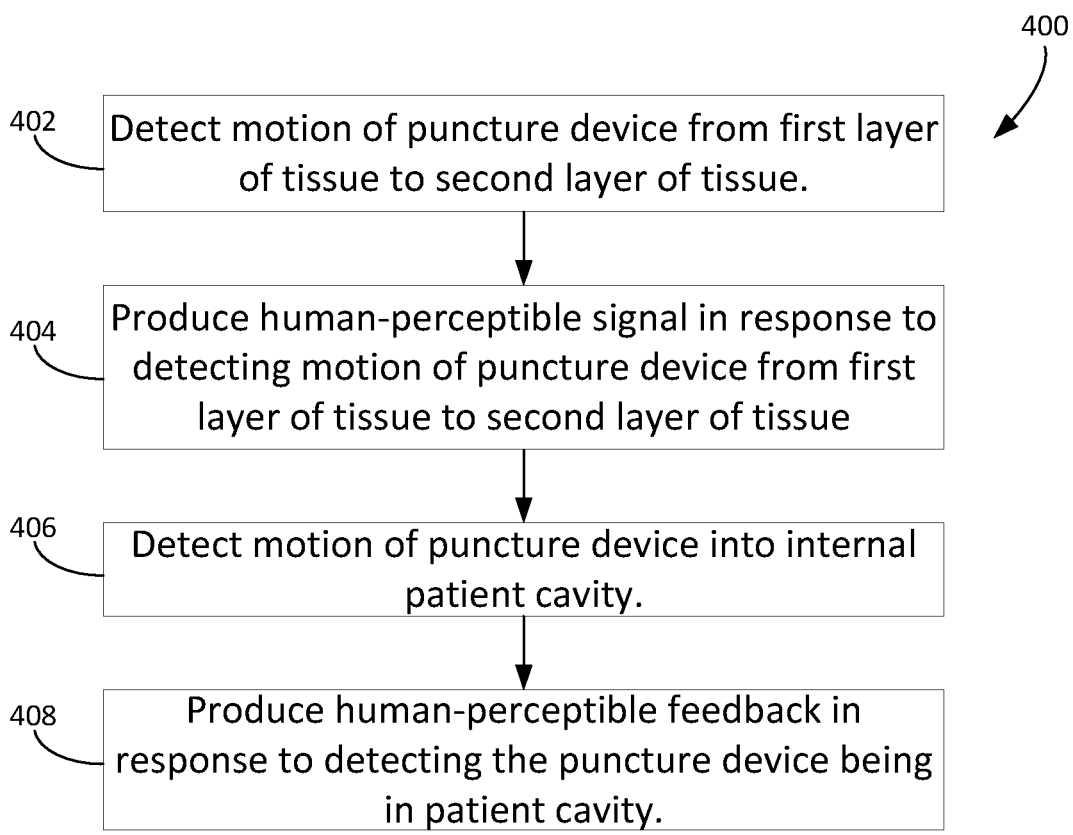
FIG. 4 is a flow chart of another process to guide insertion of a puncture device.
Figure 5A:
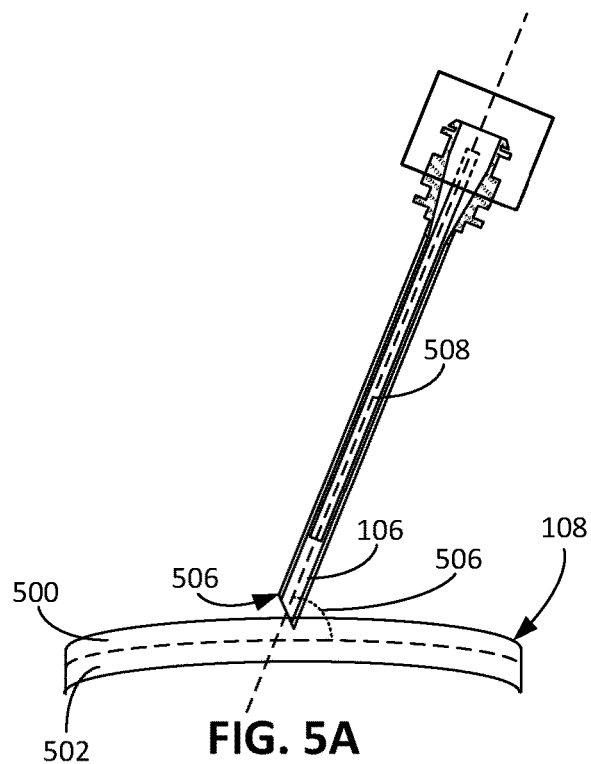
FIGS. 5A-5C depict insertion of a puncture device through tissue of a patient.
Figure 5B:
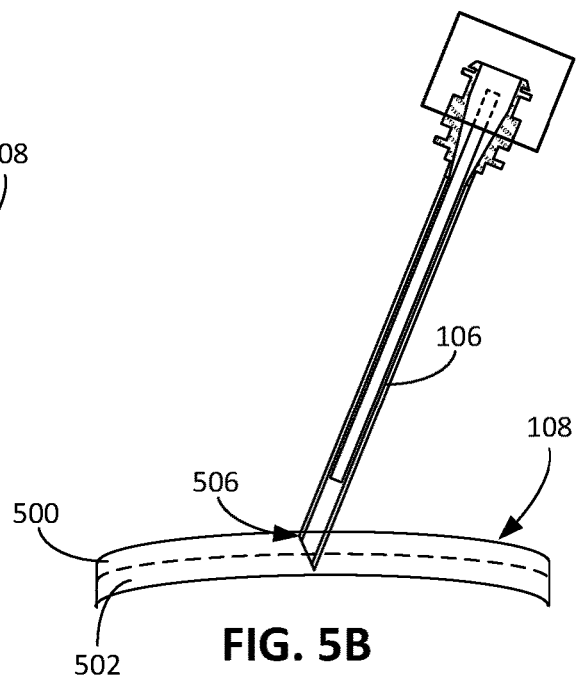

Alternatively or additionally to the process 300, the controller 114 may be configured to execute a process 400 as depicted in FIG. 4. At an operation 402, the controller 114 detects motion of the puncture device 106 from, also referring to FIGS. 5A and 5B, a first layer 500 of the tissue 108 to a second layer 502 of the tissue 108. For example, the sensor system 104 generates a signal in response to a distal portion 504 of the puncture device 106 moving from its position in the first layer 500 of the tissue 108 shown in FIG. 5A to its position in the second layer 502 of the tissue 108 shown in FIG. 5B. The first layer 500 and the second layer 502 of the tissue 108 are both positioned such that the puncture device 106 is inserted through the first layer 500 and the second layer 502 before being inserted into the cavity 110. The second layer 502 is, for example, positioned between the cavity 110 and the first layer 500. At an operation 404, the controller 114 produces the human-perceptible feedback in response to detecting motion of the puncture device 106 from the first layer 500 of the tissue 108 to the second layer 502 of tissue 108.

Figure 5C:
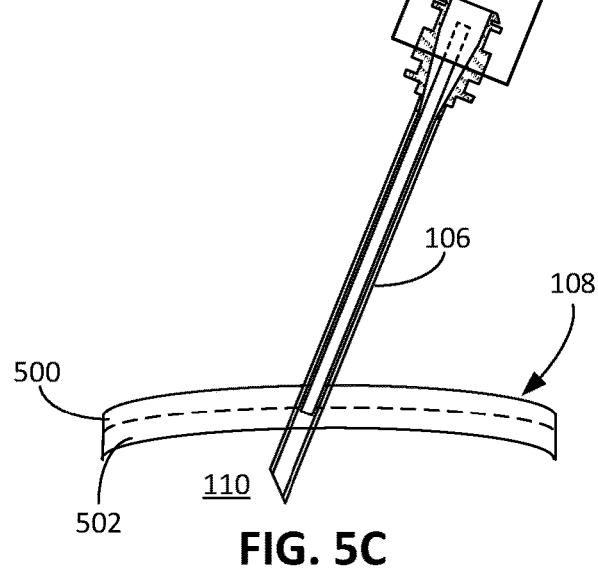

In some cases, the process 400 further includes an operation 406 in which the controller 114 detects motion of puncture device 106 into the internal patient cavity 110, as shown in FIG. 5C. The sensor system 104, for instance, generates a signal in response to the distal portion 504 of the puncture device 106 moving from its position within the tissue 108 shown in FIG. 5B to its position within the cavity 110 shown in FIG. 5C. At an operation 408, the controller 114 produces the human-perceptible feedback in response to detecting the puncture device 106 being in the cavity 110.

In some implementations, the controller 114 causes the indicator system 112 to produce both the human-perceptible feedback at the operation 408 to signify the puncture device being in the cavity 110 and the human-perceptible feedback at the operation 404 to signify motion of the puncture device 106 from the first layer 500 of the tissue 108 to the second layer 502 of the tissue 108. Other feedback methodologies may be used by other implementations. For example, in some implementations, the controller 114 causes the indicator system 112 human-perceptible feedback only in response to detecting that the puncture device is in the cavity 110. As another example, in some implementations, the controller 114 causes the indicator system 112 to produce human-perceptible feedback at points of progression of the puncture in addition to the ones shown in FIG. 4. In some cases, the controller 114 generates a wireless signal to cause the indicator system 112 to produce the human-perceptible feedback.

In some implementations, a first sensor of the sensor system 104 generates the signal in response to a distal portion 504 of the puncture device 106 moving from its position in the first layer 500 of the tissue 108 to its position in the second layer 502 of the tissue 108, while a second sensor of the sensor system 104 generates the signal in response to the distal portion 504 of the puncture device 106 moving from its position within the tissue 108 to its position within the cavity 110.

In some implementations, the controller 114 detects motion of the puncture device in response to a signal generated by a sensor system monitoring a parameter associated with the insertion. The signal is, in some cases, a portion of a stream of signal output from the sensor system 104 that is indicative of the sensed characteristic, such as a particular signal waveform in a larger signal data stream. The signal may also be a discrete signal. The signal may be indicative of the motion of the puncture device 106 through the tissue into the cavity 110 by indicating the actual motion by tracking a characteristic such as position, velocity, or acceleration. Alternatively or additionally, the signal may be indicative of motion of the puncture device 106 through the tissue into the cavity 110 by indicating a result of the motion, such as a distal end of the puncture device 106 being in the cavity 110.

The signal indicative of motion of the puncture device 106 generated by the sensor system 104 is, for example, indicative of a change in a parameter monitored by the sensor system 104. The change in the parameter is indicative of motion of the distal portion 504 of the puncture device 106 from the tissue 108 into the cavity 110, e.g., the puncture device 106 being in the cavity 110. In some cases, the change in the parameter is indicative of motion of the puncture device 106 relative to the tissue 108, relative to the cavity 110, relative to a surface in an environment of the insertion system 100, and/or relative to another reference point in the environment. As described herein, the sensor system 104 generates a signal indicative of a change in a force, a pressure, a sound, an electrical characteristic, or other appropriate parameter. Rather than monitoring the parameter, in other implementations, the sensor system 104 alternatively or additionally generates the signal in response to an event. In this regard, the controller 114 detects motion of the puncture device in response to a signal generated by a sensor system that responds to the event. The sensor system 104, absent the occurrence of the event, does not generate the signal. In some examples, the event corresponds to a change in a parameter being greater than a predefined value. In some examples, the event corresponds to motion of the puncture device 106 from a first layer of tissue 108 to a second layer of the tissue 108. In some examples, the event corresponds to motion of the puncture device 106 from the tissue 108 into the cavity 110, e.g., the puncture device 106 being in the cavity 110. Examples of variations of sensor systems and parameters, e.g., parameters to which the sensor systems are responsive or parameters measured by the sensor systems, are discussed with respect to FIGS. 11-17 as well as elsewhere herein.

In some cases, the indicator system 112 generates the human-perceptible feedback to guide the motion of the puncture device 106. In some cases, the feedback guides the motion such that the puncture created by the puncture device 106 is appropriately positioned for a surgical operation to be performed using the surgical tool. The human-perceptible feedback includes visual feedback, audio feedback, tactile feedback, or other appropriate human-perceptible feedback to guide motion of the puncture device 106 controlled by the human operator. When the human-perceptible feedback includes visual feedback, the indicator system 112 can include an indicator light, a display, and/or other visual indication device to generate the visual feedback. When the human-perceptible feedback includes audio feedback, the indicator system 112 can include a speaker and/or other audio generation devices to generate the audio feedback. When the human-feedback system includes tactile feedback, the indicator system 112 can include a vibrator, a motor, a brake for locking motion of the puncture device, a drive system operable to control movement of the puncture device, and/or other tactile indication or haptic feedback devices to generate the tactile feedback. In some implementations, the indicator system 112 forms part of the insertion system 100, e.g., the indicator system 112 is an indication device on the insertion system 100. In some implementations, the indicator system 112 is an external indication device in communication with the controller 114.

In some implementations, the human-perceptible feedback is produced based on information in addition to the information represented by the signal generated by the sensor system 104. The indicator system 112 is, for instance, operable by the controller 114 based on information input by an operator. In some cases, the information input by the operator includes patient information. The patient information is indicative of, in some cases, a physical characteristic of the patient, such as a size, a weight, a geometry, a thickness of the patient tissue, health history such as previous history of smoking, or other physical characteristic. The patient information includes, for example, data representing an image of a region of the patient including the tissue 108 and the cavity 110. Such data may be the image itself, or information derived from the image such as number of tissue layers and thickness of patient tissue. This data representing the image may be acquired before or during the procedure. For example, in some cases, before the puncture device 106 is inserted through the tissue 108, an x-ray machine, a computed tomography (CT) scanner, a magnetic resonance imaging (MRI) machine, or other medical imaging device captures the image.

In some implementations, the additional patient information is indicative of the procedure, such as a location of an insertion site for the puncture to be made by the puncture device 106, the type of surgery planned, a posture of the patient, etc. Based on the location of the insertion site, the controller 114, in some examples, estimates a thickness of the tissue 108 to be punctured and provides operator feedback in view of the estimated thickness. Based on the location of the insertion site, the controller 114, in some cases, determines a location of an anatomical feature that should be avoided. Types of anatomical features may vary depending on the region of the patient that the surgical operation is to be performed. For example, potential anatomical features to be avoided include solid vital organs, tissue adhesions, and vessels. The controller 114 accordingly provides the human-perceptible feedback such that the puncture device 106 is kept a predefined distance from the anatomical feature.

In some cases, the information includes information indicative of a keepout or protected volume in which the puncture device 106 is prohibited from entering. In some implementations, the keepout volume is entirely within the patient, whereas in other implementations, the keepout volume extends beyond an exterior surface of the patient. The keepout volume can be selected to ensure that locations of certain anatomical features are avoided. In some implementations, the keepout volume is selected by the controller 114 based on one or more signals generated by the sensor system 104. For example, a medical imaging device can capture imagery of the patient, and this imagery can be used by the controller 114 to determine a keepout volume. Based on distinctive features in the imagery, e.g., bony landmarks such as the hip bone or the sternum, the controller 114 determines locations of various anatomical features of the patient. The controller 114 can then determine a keepout volume for the puncture device 106 based on the locations of these anatomical features. The keepout volume can encompass the locations of the anatomical features and can extend beyond the anatomical features to provide a buffer space between an outer boundary of the keepout volume and the anatomical features. In some implementations, the keepout volume is adjusted in real-time based on real-time sensor signals generated as the puncture device 106 is moved for creating the puncture. The keepout volume can be adjusted as the sensor system 104 detects an anatomical feature during the movement of the puncture device 106. For example, if the sensor system 104 detects an anatomical feature as the puncture device 106 travels through the tissue 108, the keepout volume is adjusted to encompass the anatomical feature. Alternatively or additionally, an operator selects the keepout volume on a user interface. For example, the user interface can present imagery of the patient, and the operator can manually indicate which portions of the patient should be avoided by the puncture device 106.

The thickness of layers of tissue can vary depending on the site for insertion of the puncture device 106. In some cases, the tissue 108 is thinner. The tissue 108, for example, lacks muscle. If the insertion site is, for example, the umbilicus, the lack of muscle in the umbilicus results in thinner tissue relative to other insertion sites. The puncture device 106 travels a lower distance through the tissue 108 to be inserted into the cavity 110 of the patient, e.g., for the puncture device 106 to be in the cavity 110. In some cases, the type of layers of tissue can influence an amount of resistance expected as the puncture device 106 is inserted into the tissue. Insertion sites that may include layers of tissue with higher resistance include, for example, the anterior rectus sheath, posterior rectus sheath, peritoneum.

Alternatively or additionally, the information input by the operator includes information indicating a surgical operation to be performed on the patient. In some examples, the surgical operation to be performed on the patient indicates the cavity 110 to which the puncture device 106 is to be used to provide access. In some examples, the information indicating the surgical operation to be performed provides information pertaining to the tissue 108 overlying the cavity 110, e.g., a thickness, elasticity, strength, type of the tissue 108. In some examples, the information indicating the surgical operation to be performed provides information pertaining to the cavity 110, e.g., a size, a depth, a length, a width, or other geometry of the cavity 110. In some cases, the operator input includes information indicative of a compliance of patient tissue defining the cavity 110. If, for example, the patient cavity corresponds to a cavity surrounding a joint, the information can indicate that the tissue includes stiff tissue, e.g., cartilage or bone, that would cause the puncture device 106 to experience greater resistance to insertion than compared to, for example, muscle tissue.

In some cases, the surgical operation is a laparoscopic surgical operation to be performed in the peritoneal cavity of the patient. In this regard, the cavity 110 corresponds to the peritoneal cavity, and the puncture device 106 is inserted through the tissue 108 to provide the surgical tool with access to the peritoneal cavity. In some cases, the surgical operation is a lung biopsy, and the cavity 110 corresponds to a thoracic cavity within which the patient's lung is positioned. The puncture created by the puncture device 106, for example, enables a biopsy tool to access the patient's lung. In some implementations in which a biopsy is to be performed, the biopsy tool includes an end effector to be operated to collect a portion of tissue from the lung when the biopsy tool is positioned within the thoracic cavity. In some implementations, the puncture device 106 is inserted through the tissue 108 to provide access to a vascular system of the patient. In some implementations, the puncture device 106 is inserted to provide access to a joint of the patient, e.g., for an orthopedic surgical operation. The puncture device 106 is inserted, for example, such that it penetrates into a joint capsule of the joint at which the surgical operation is to be performed using the surgical tool. In some implementations, the puncture device 106 is inserted to provide access to a surgical tool to an internal patient cavity such that the surgical tool can be used to perform an ophthalmic surgical operation. The puncture device 106 is, for example, inserted to penetrate the sclera of the patient. In some implementations, the puncture device 106 is inserted to enable a surgical tool to perform a cranial surgical operation. The puncture device 106 is used, for example, to penetrate the skull.

In some implementations, the insertion system 100 corresponds to a module attachable to the puncture device 106. The module includes a housing that supports the sensor system 104 and the puncture device holder 102. The puncture device holder 102, for example, is attachable to the puncture device 106, and, when the puncture device holder 102 is attached to the puncture device 106, the sensor system 104 is capable of generating signals in response to motion of the puncture device 106 through the tissue 108. The puncture device 106 is mounted to the insertion system 100, e.g., by an operator, prior to insertion of the puncture device 106 through the tissue 108. In some cases, the insertion system 1100 includes the puncture device 106, e.g., the puncture device 106 is integral to the insertion system 100. In some cases, the module includes an electrical connector to be electrically connected to the controller 114. The controller 114 is, for example, a controller external to the insertion system 100 and is capable of operating the indicator system 112 when the module is electrically connected to the controller 114. In some cases, the housing of the module supports the controller 114, and the controller 114 is electrically connected to the sensor system 104.

The puncture device 106 includes, in various implementations for example, a needle, a trocar, an obturator, a cannula, and/or other devices operable to create the puncture. The distal portion 504 of the puncture device 106 is, for example, a sharp implement that creates an incision through human tissue when the puncture device 106 contacts the tissue with sufficient force. In some implementations, the puncture device 106 is hollow to enable an elongate tool to be inserted through the puncture device 106. The elongate tool, for example, forms a portion of the sensor system 104. In cases in which the puncture device 106 is hollow, fluid can be ejected through the puncture device 106, e.g., from a proximal portion of the puncture device 106 toward a distal portion of the puncture device 106. In some implementations, the fluid comprises a gas such as air, a liquid such as saline, or the like. In some implementations, the puncture device 106 is a Veress needle including a blunt and retractable obturator and a trocar shield component.

In some implementations, the puncture device 106 is a trocar including a cannula to create the puncture and an obturator extendible through the cannula. In some implementations, the puncture device 106 is inserted through the tissue 108 and into the cavity 110 to create the puncture, and a port device is inserted into the puncture to support the tissue 108 and to form an access port to the cavity 110 through which the surgical tool is inserted into the cavity 110. Alternatively, the puncture device 106 includes the port device. The puncture device 106 includes, for instance, an obturator inserted through a port of the cannula, and is used to create an initial puncture through the tissue 108 and into the cavity 110. Removal of the obturator from the cannula after the initial puncture provides a port through the cannula. The port device is then positioned through the incision to support the tissue 108 and to form the access port to the cavity 110. In some cases, the initial puncture is enlarged by one or more incisions to enable insertion of the port device into the enlarged incision, or to enable a surgical tool of a predefined size to be inserted through the enlarged incision. The cannula is, in some cases, removed after the port device forms the access port to the cavity 110.

Example Surgical Systems and Related Methods

Figure 6:
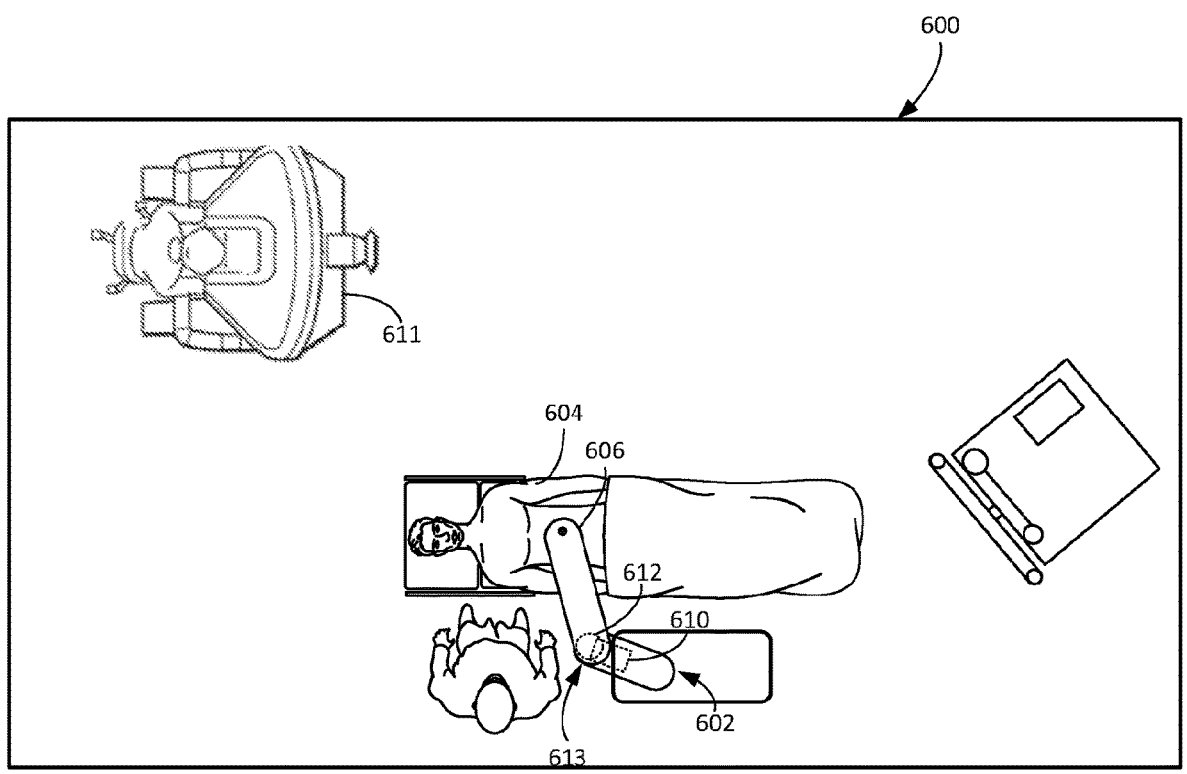
FIG. 6 is a schematic top view of a surgical system.

The surgical puncture device insertion systems described herein can be part surgical systems, e.g., telesurgery systems. In certain examples as shown in FIG. 6, operator or operators operate a surgical system 600 including a remotely controllable manipulator 602 to perform a surgical operation on a patient 604. The remotely controllable manipulator 602 supports a puncture device, e.g., the puncture device 106 of FIG. 1. The remotely controllable manipulator 602 may include a puncture device holder (e.g., the puncture device holder 102 of FIG. 1) that is particularly configured for holding the puncture device or that is for other use as well such as for holding surgical instruments. A distal portion 606 of the remotely controllable manipulator 602 supports the puncture device 106. In some examples in which the insertion system 100 corresponds to a module to be attached to the puncture device 106, the remotely controllable manipulator 602 supports the insertion system 100 and its associated components. The remotely controllable manipulator 602, for instance, supports the puncture device 106 when the puncture device 106 is attached to the insertion system 100.

The remotely controllable manipulator 602 includes a drive system 610 connected to a joint 613 of the remotely controllable manipulator 602. Referring briefly to the example shown in FIGS. 10A-10D, in some cases, the remotely controllable manipulator 602 includes multiple joints to be driven by the drive system 610. The drive system 610 is operable to control motion of the remotely controllable manipulator 602. In this regard, when the puncture device 106 is supported by the remotely controllable manipulator 602, the drive system 610 is operable to control motion of the puncture device 106.

If the surgical system 600 is a telesurgery system, the surgical system 600 includes a console 611 operable by a surgeon. The surgeon operates the console 611 to control the remotely controllable manipulator 602, e.g., to control the drive system 610 of the remotely controllable manipulator 602 during a surgical operation. The surgeon, for example, operates the surgeon's console 611 to manipulate a surgical tool mounted to the remotely controllable manipulator 602. Various surgical tools can be mounted onto the remotely controllable manipulator 602 during the surgical operation. In some implementations, the console 611 is positioned within a surgical environment. Alternatively, the console 611 is positioned at a remote location outside of the surgical environment. The console 611 is usable by the surgeon to perform a minimally invasive telesurgery.

In some implementations, the console 611 includes a display to enable the surgeon to view a surgical site through images captured by an imaging device. The display is, for example, a stereoscopic display that shows stereoscopic images of the surgical site. While viewing the images of the surgical site, the surgeon performs the surgical operation on the patient by manipulating control input devices on the console 611. The console 611 in turn generates signals to control motion of the remotely controllable manipulator in accordance with the instructions represented by the surgeon's manipulations of the control input devices Alternatively or additionally, the remotely controllable manipulator 602 includes a sensor system 612 coupled to the remotely controllable manipulator 602, e.g., operable to detect motion of the joint 613, operably connected to the joint 613, physically coupled to the remotely controllable manipulator 602. The sensor system 612 generates a signal based on a parameter associated with the joint 613. In some implementations, the sensor system 612 monitors the parameter associated with the joint 613. The sensor system 612, for example, generates the signal in response to a force applied to the joint 613, a torque applied to the joint 613, a motion (e.g. position or derivatives of position such as velocity and acceleration) of the joint 613, an indication of any of the above such as an amount of electrical current or voltage, and the like. The force or torque applied to the joint 613 is, for example, caused by a force or a torque on the distal portion 606 of the remotely controllable manipulator 602. When the distal portion 606 of the remotely controllable manipulator 602 supports the puncture device 106, a force or a torque on the puncture device 106, e.g., caused by contact with patient tissue, can be transferred to the joint 613 such that the signal generated by the sensor system 612 is indicative of the force or the torque on the puncture device 106. The sensor system 612 is, for example, an encoder, an accelerometer, a force sensor, a torque sensor, or other appropriate sensor to measure force or torque applied to the joint 613 or other appropriate parameter associated with the joint 613.

Alternatively or additionally, the insertion system is connected to the surgical system such that the feedback is provided to the operator through the console 611. For example, a surgeon using the console 611 can receive feedback through the console 611. The console 611, for instance, receives the signal generated by the sensor system 612 and/or presents the feedback to the operator to guide the insertion of the puncture device 106.

Figure 7:
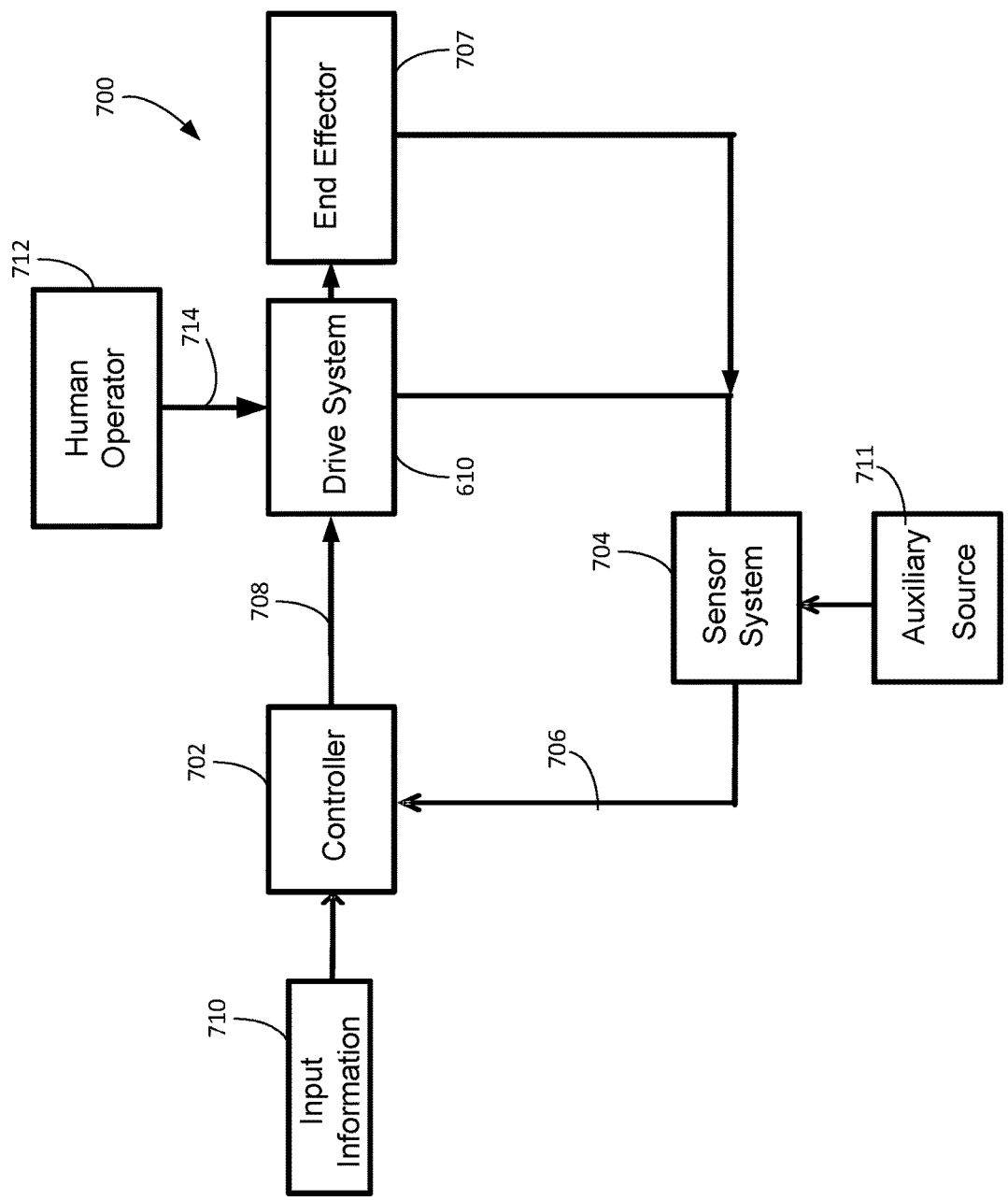
FIG. 7 is a block diagram representing a feedback process.

Also referring to an example of a process 700 depicted by the block diagram in FIG. 7 that can be used with the surgical system 600, the surgical system 600 includes a controller 702 and a sensor system 704, e.g., including the sensor system 612, that generates a signal 706 indicative of motion of the puncture device 106 through the tissue 108 into the cavity 110. The controller 702 is operably connected to the sensor system 704 such that the controller 702 receives the signal 706 generated by the sensor system 704. The controller 702 is configured to operate the drive system 610, for example, to control movement of an end effector 707 mounted to the remotely controllable manipulator 602. The controller 702 operates, for instance, the drive system to control movement of the puncture device 106 as the puncture device 106 is inserted through the patient's tissue and cavity.

The process 700 is a feedback process in which a control signal 708 is generated based in part on a feedback signal, e.g., the signal 706 from the sensor system 704. The sensor system 704 generates the signal 706 in response to an event or a parameter associated with the drive system 610 and/or the end effector 707. In the feedback process, the signal 706 is, for example, representative of a parameter that the controller 702 uses to generate the control signal 708 to maintain the signal 706 within a predefined range. The parameter is, for example, a position, an angle, a velocity, an acceleration, a force, a torque, or other parameter associated with the end effector 707 and/or the remotely controllable manipulator 602. In some examples, the sensor system 704 generates the signal 706 as a function operation of an auxiliary device 711. For example, as described with respect to FIG. 16, the auxiliary device 711 can be a stabilizing device operable to stabilize tissue, an insufflator that generates a fluid pressure detected by the sensor system 704. The sensor system 704 can correspond to any sensor system described herein, for example, one of the sensor systems described with respect to FIGS. 11-17 as well as elsewhere herein. In addition, the parameter to which the sensor system 704 is responsive corresponds to any parameter discussed herein.

While human perceptible feedback is described herein as being generated in response to a sensor signal of a sensor system, alternatively or additionally, the puncture device 106 is autonomously moved in response to the sensor signal. For example, based on the feedback signal from the sensor system 704, the controller 114 generates the control signal 708 to inhibit movement of the puncture device 106 when the parameter is outside of the predefined range. The controller-facilitated control of movement of the puncture device 106 can reduce the risk of human error associated with awaiting operator response to human perceptible feedback. In some implementations, the controller 114 operates movement of the remotely controllable manipulator 602 based on an input information 710 in addition to the signal 706 from the sensor system 704. The predefined range for the parameter measured by the sensor system 704 is, for example, defined by the additional input information 710. This additional input information 710 corresponds to, for example, an operator input as described herein. In some cases, the operator input includes the patient information, the surgical operation information, or other information relevant for controlling movement of the puncture device 106 through the tissue and the cavity of the patient.

Based on the input information 710, the sensor signals generated by the sensor system 704, or a combination of both of these, the controller 711 can control autonomous movement of the puncture device 106. The input information 710 and the sensor signals can be indicative of information similar to the information described herein as being used for generating the human-perceptible feedback. For example, a keepout volume could be selected based on the input information 710 and the sensor signals. The controller 711 can control movement of the puncture device 106, based on the keepout volume, to inhibit the movement of the puncture device 106 into the keepout volume while guiding the creation of the puncture by the puncture device 106. With the keepout volume, the puncture device 106 can be controlled to avoid sensitive anatomical features. The movement of the puncture device 106 can be adjusted such that the puncture device 106 is inserted through the tissue without moving into the keepout volume.

In some implementations, a human operator 712 applies a force input 714 on the drive system 610. The force input 714, for instance, influences movement of the drive system 610, in turn, influencing movement of the end effector 707 and influencing the signal 706 generated by the sensor system 704.

In some examples, the controller 114 generates the control signal to operate a motor of the drive system 610 associated with the joint 613 to cause movement of the remotely controllable manipulator 602. Movement of the remotely controllable manipulator 602, when the surgical tool is mounted on the remotely controllably manipulator, causes motion of the surgical tool. The controller 702 operates the drive system 610 as a function of the signal 706 generated by the sensor system 704. In particular, the controller 702 operates the drive system 610 to guide motion of the surgical tool supported by the remotely controllable manipulator 602. The surgical tool is, for example, the puncture device 106, and the controller 702 operates the drive system to guide motion of the puncture device 106 through the tissue and into the cavity, thereby creating the puncture. The controller 702 then operates the drive system 610 to insert the surgical tool into the puncture created by the puncture device 106.

In certain examples, the controller 702 corresponds to the controller 114 of the insertion system in block diagram 200 (shown in FIG. 2). In certain examples, the insertion system of block diagram 200 includes the drive system 610, and the sensor system 704 of the surgical system 600 includes the sensor system 104 of the insertion system 100. In some examples, the controller 702 corresponds to a controller of the remotely controllable manipulator 602. While FIG. 2 depicts the drive system 610 and the indicator system 112 to be separate systems, in some cases, the indicator system 112 includes the drive system 610. The controller 114 operates the drive system 610 to generate human-perceptible feedback, e.g., tactile feedback, in response to the signal from the sensor system 704. In some examples, the indicator system 112 corresponds to an indicator system of a patient-side cart including the remotely controllable manipulator 602. The indicator system 112 in such a case includes, for instance, a display that produces the human-perceptible feedback for the operator.

Figure 8:
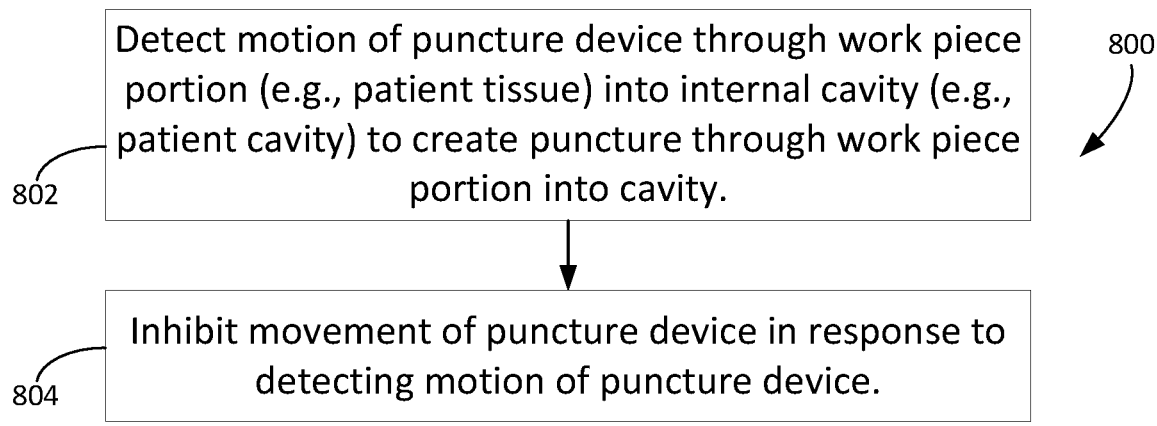
FIG. 8 is a flow chart of a process to inhibit motion of a puncture device.

FIG. 8 is a flow chart depicting an example of a process 800 that can be used with the insertion system 100, surgical system 600, and other systems described herein to guide insertion of a puncture device, e.g., the puncture device 106, and to be performed by a controller, e.g., the controller 702. At an operation 802, the controller 702 detects motion of the puncture device 106 through patient tissue into internal patient cavity to create the puncture through the tissue into the cavity. At an operation 804, the controller 702 inhibits movement of the puncture device in response to detecting motion of puncture device 106.

Figure 9:
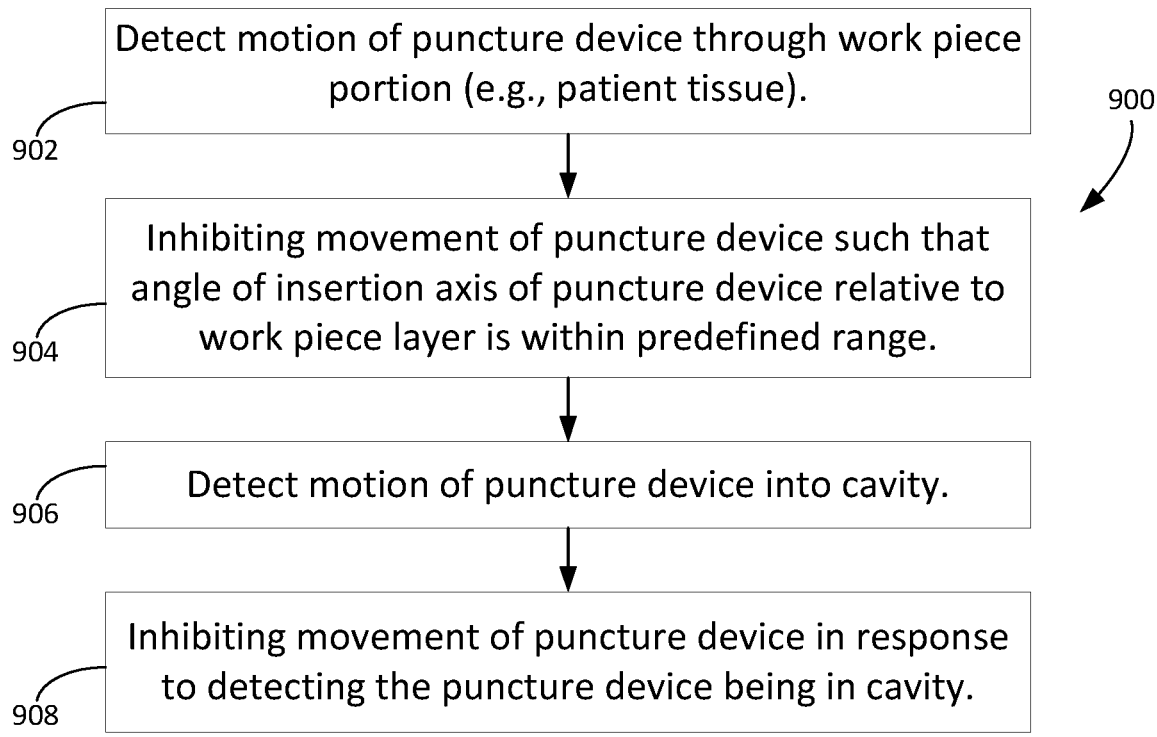
FIG. 9 is a flow chart of another process to inhibit motion of puncture device.
Figure 10A:
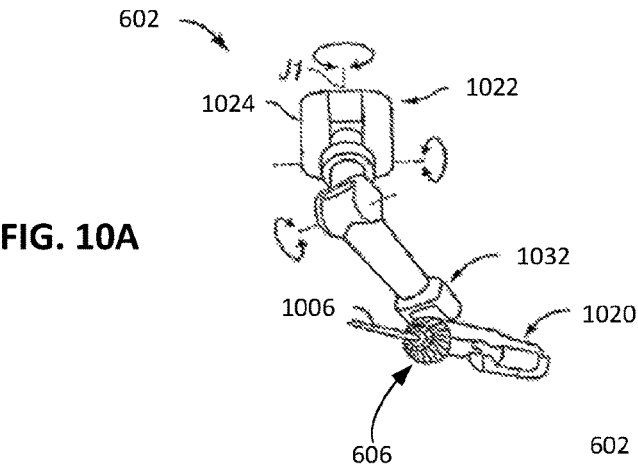
FIGS. 10A-10C are bottom, side, and back views, respectively, of a remotely controllable manipulator with an instrument.
Figure 10B:
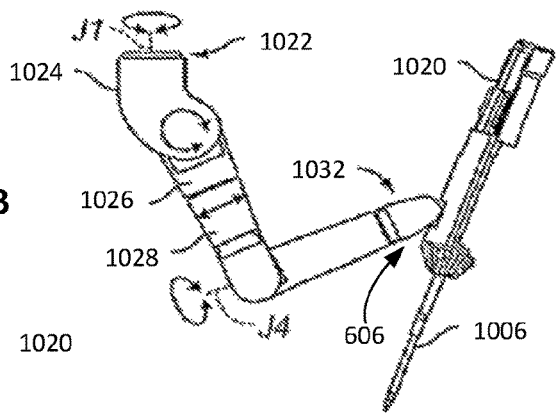
Figure 10C:
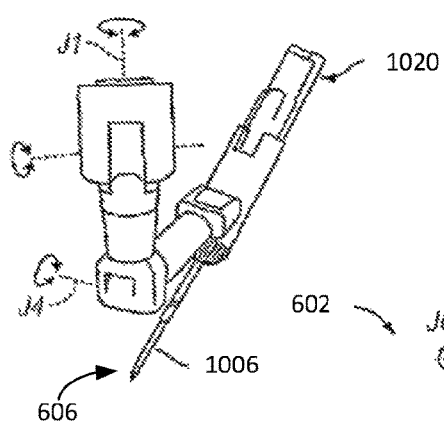
Figure 10D:
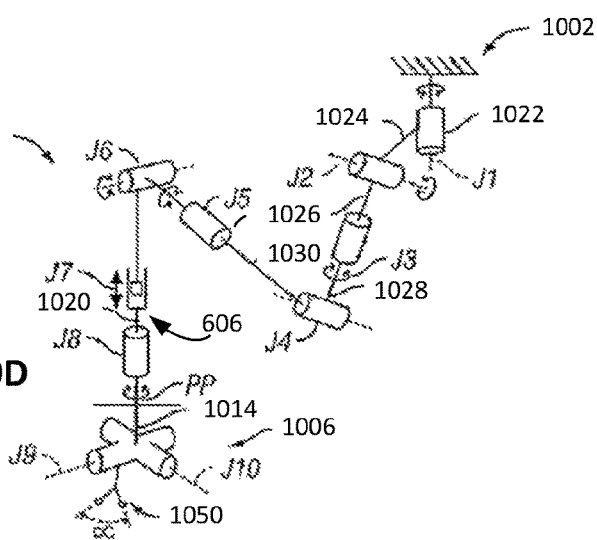
FIG. 10D is a schematic diagram of the remotely controllable manipulator and instrument of FIGS. 10A-10C.
Figure 11:
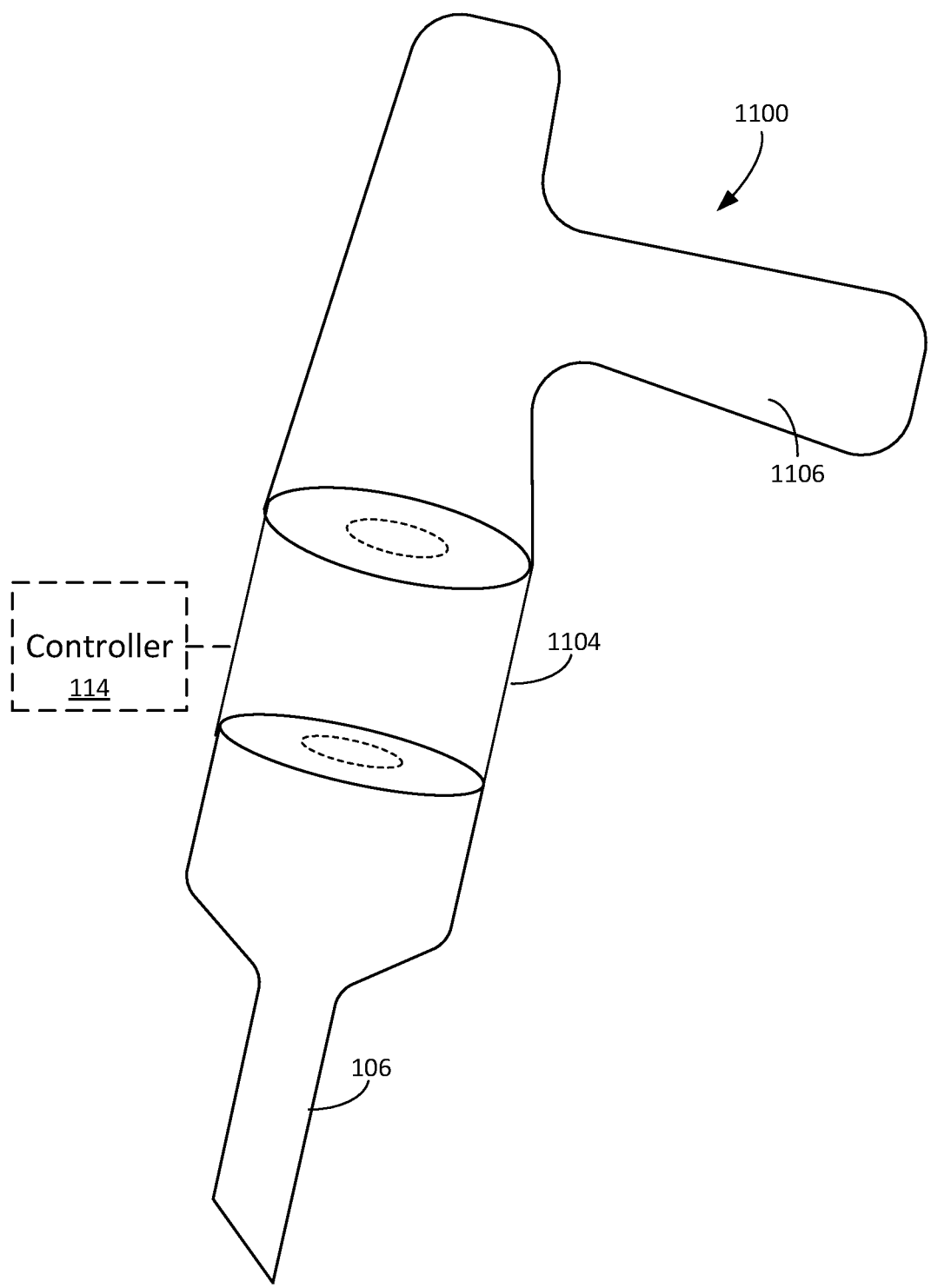
FIG. 11 is a side view of a surgical puncture device insertion system including a force sensor.
Figure 12:
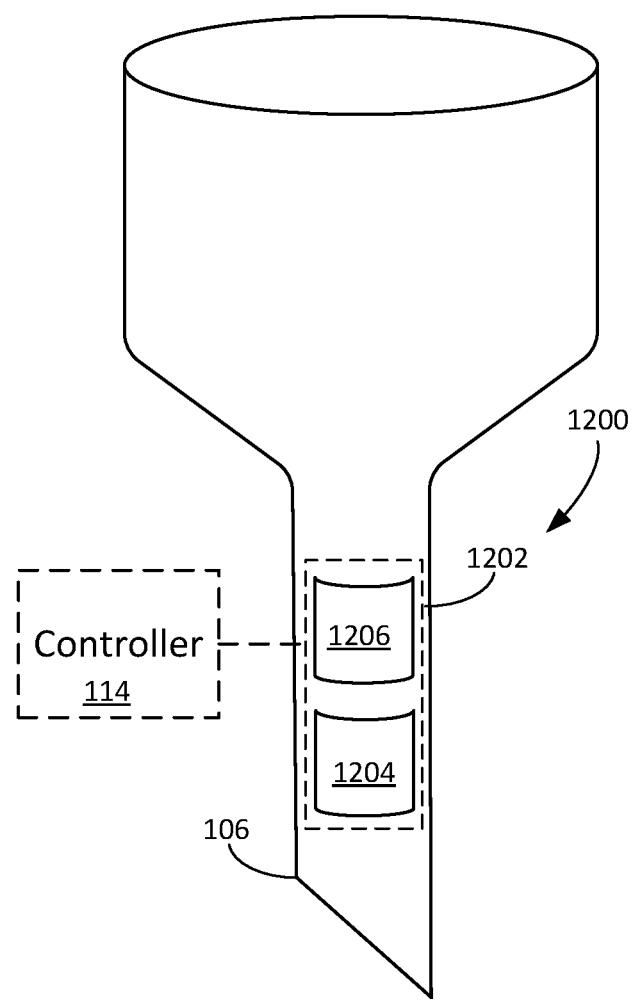
FIG. 12 is a side view of a surgical puncture device insertion system including an optical sensor.
Figure 13:
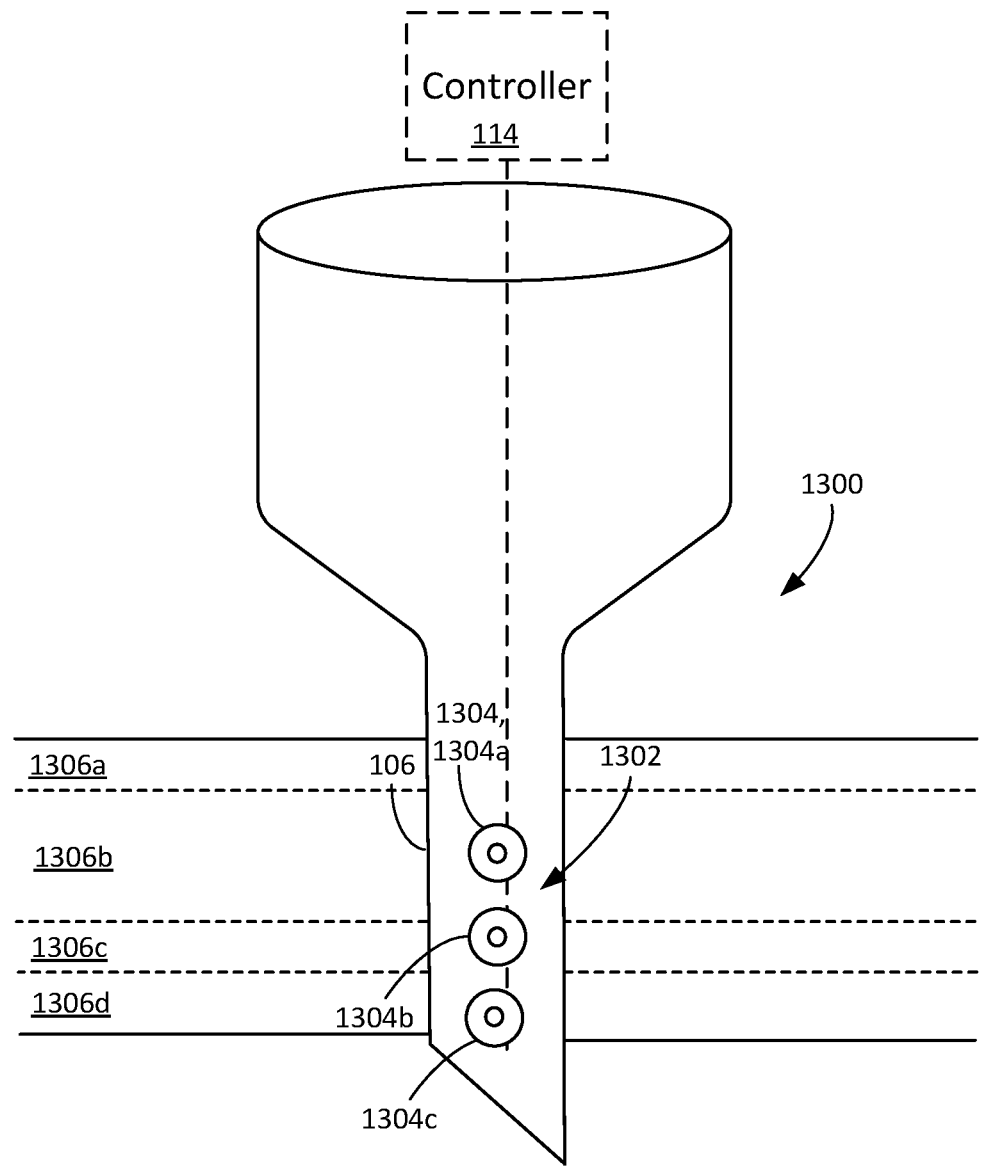
FIG. 13 is a side view of a surgical puncture device insertion system including an electrical characteristic sensor.
Figure 14:
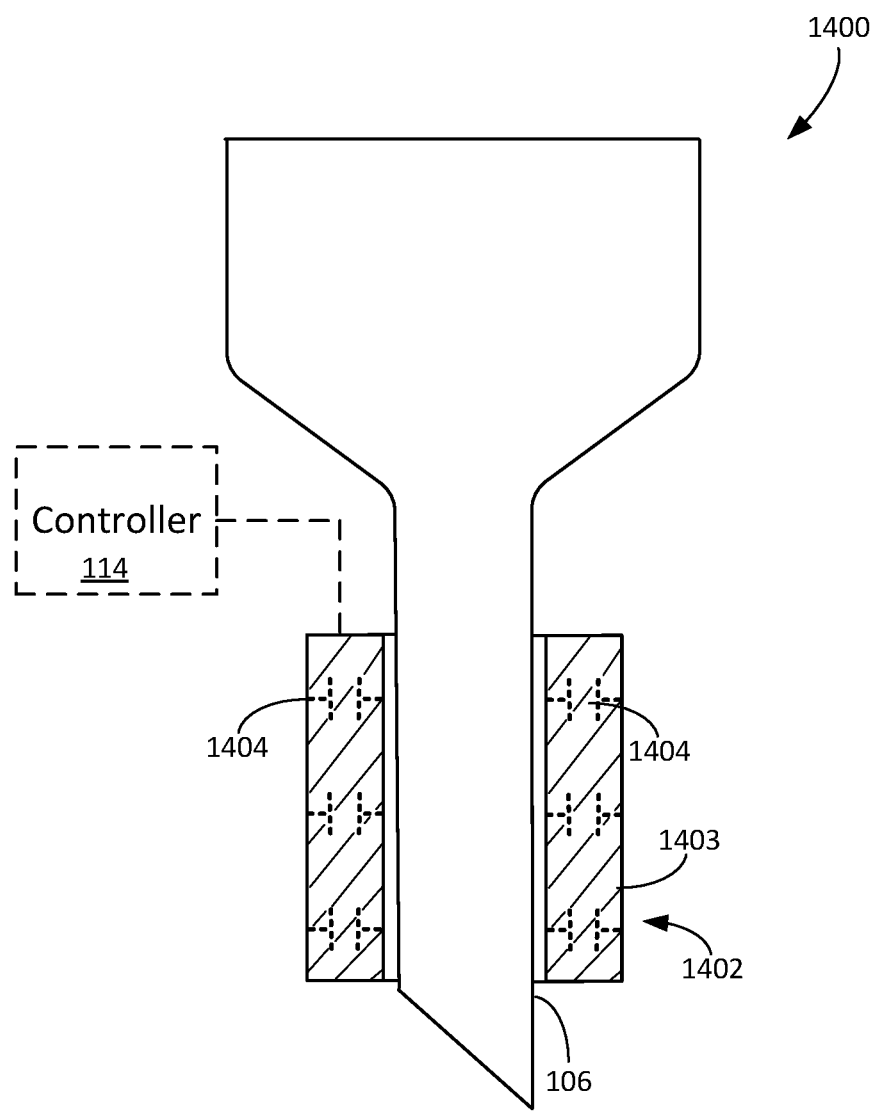
FIG. 14 is a side view of a surgical puncture device insertion system including a capacitance sensor.
Figure 15:
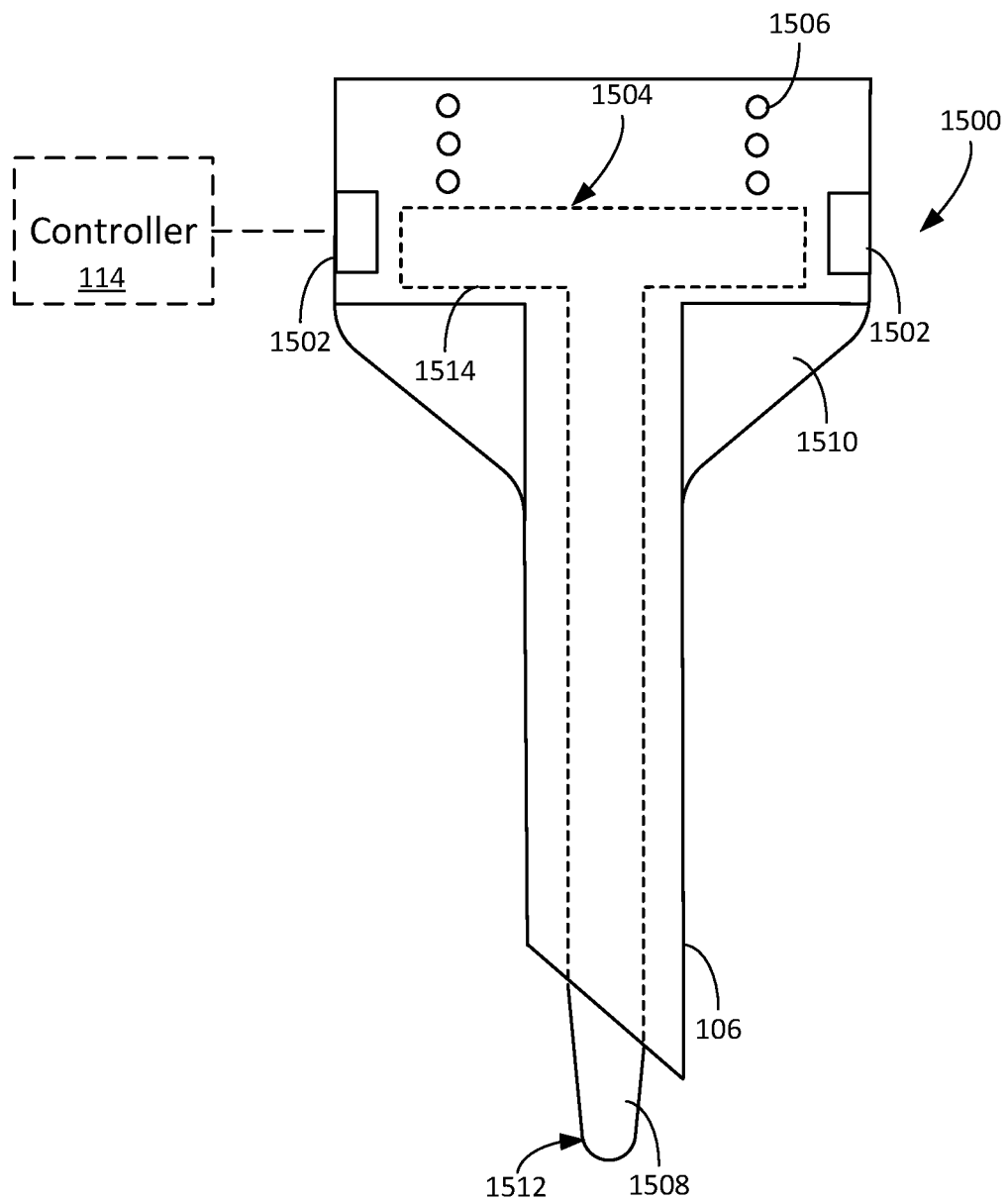
FIG. 15 is a side view of a surgical puncture device insertion system including an audio receiver.

FIG. 9 is a flow chart depicting an example process 900 that can be used with the insertion system 100, surgical system 600, and other systems described herein to guide insertion of a puncture device, e.g., the puncture device 106, and to be performed by a controller, e.g., the controller 702. At an operation 902, the controller 702 detects motion of the puncture device 106 through the tissue 108. At an operation 904, the controller 702 inhibits movement of the puncture device 106 such that, referring back to FIG. 5A, an angle 506 of an insertion axis 508 of the puncture device 106, e.g., relative to the tissue 108, is within a predefined range. Alternatively or additionally, at an operation 906, the controller 702 detects motion of the puncture device 106 into the cavity 110. At an operation 908, the controller 702 inhibits movement of the puncture device 106 in response to detecting motion of the puncture device 106 into the cavity 110, e.g., the puncture device 106 being in the cavity 110.

In some implementations, the angle is selected such that the insertion axis 508 does not intersect with sensitive patient anatomy, e.g., such that the puncture device 106, as it is being inserted into the cavity 110, does not contact the sensitive patient anatomy. For instance, in some cases, if the puncture device 106 is to be inserted through the umbilicus, the angle is maintained within a predefined range based on a location of the aorta, e.g., the aorta bifurcation. The puncture device 106 is, for example, maintained within a range of about 45 degrees caudad along the sagittal plane. The puncture device is, for example, maintained within a range of about 90 degrees to the body wall tissue in obese patients, e.g., patients having a body mass index (BMI) greater than 30. In some implementations, the predefined range is an operator input selected prior to inserting the puncture device 106.

In some cases, the controller 702 detects the motion of the puncture device 106 at operations 802, 902, and/or 906 based on a signal from a sensor of the sensor system 704. In some cases, the controller 702 operates a motor, a brake, or other device of the drive system 610 at operations 804, 904, and/or 908 to inhibit movement of the remotely controllable manipulator 602, and thereby inhibit movement of the puncture device 106. In some cases, the process 800 includes the process 900. The operation 802 includes, for example, the operation 902 of the process 900 and/or the operation 906 of the process 900. The operation 804 includes, for example, the operation 904 of the process 900 and/or the operation 908 of the process 900.

In some implementations, as shown in the bottom, side, and back views of the remotely controllable manipulator 602 of FIGS. 10A-10D, respectively, where the remotely controllable manipulator 602 is coupled with a surgical tool 1006. The remotely controllable manipulator 602 is operable to move the surgical tool 1006 relative to a base 1002 of the remotely controllable manipulator 602. An instrument holder 1020 at the distal portion 606 of the remotely controllable manipulator 602 supports the surgical tool 1006. In some implementations, when the puncture device 106 is being inserted into the patient, the surgical tool 1006 corresponds to, for example, the puncture device 106 and/or the insertion system 100. In this regard, the instrument holder 1020 is configured to support the puncture device 106. In such implementations, the instrument holder 1020 is also configured to support a surgical tool for performing a surgical operation after the puncture device 106 is used to create the puncture through the patient tissue. Because a number of different surgical tools having differing end effectors may be sequentially mounted on each remotely controllable manipulator 602 during a surgical operation, the instrument holder 1020 can allow for rapid removal and replacement of the mounted surgical tool 1006.

In some implementations, when the puncture device 106 is being inserted into the patient, the remotely controllable manipulator 602 does not hold the surgical tool 1006 and some other part of the remotely controllable manipulator 602 may support the puncture device 106. In some implementations, when the puncture device 106 is being inserted into the patient, the remotely controllable manipulator 602 holds the surgical tool 1006, and the surgical tool 1006 holds the puncture device 106.

In some implementations, the remotely controllable manipulator 602 includes multiple joints having degrees of freedom to enable movement of the surgical tool 1006 mounted to the distal portion 606 of the remotely controllable manipulator 602. Each of the joints may include a corresponding motor and/or brake. The remotely controllable manipulator 602 is, for example, mounted to the base 1002 by a pivotal mounting joint 1022 so as to allow the portion of the remotely controllable manipulator 602 distal to the pivotal mounting joint 1022 to rotate about a first joint axis J1. In the example shown in FIGS. 10A-10D, the mounting joint 1022 provides rotation about a vertical axis. The base 1002 and the mounting joint 1022 are positioned at a proximal portion of the remotely controllable manipulator 602. A first link 1024 extends distally from the base 1002 and rotates about first pivotal joint axis J1 at joint 1022. A distal end of the first link 1024 is coupled to a proximal end of a second link 1026 at a joint providing a horizontal pivotal axis J2. A proximal end of a third link 1028 is coupled to the distal end of the second link 1026 at a roll joint so that the third link generally rotates or rolls at joint J3 about an axis extending along and, in some cases, aligned with axes of both the second and third links. Distal to the pivotal joint J4, the distal end of a fourth link 1030 is coupled to the instrument holder 1020 by a pair of pivotal joints J5, J6 that together define an instrument holder wrist 1032. A translational or prismatic joint J7 of the remotely controllable manipulator 602 facilitates axial movement of the surgical tool 1006 and the elongate shaft 1014 of the surgical tool 1006 through the minimally invasive aperture, and also facilitates attachment of the instrument holder 1020 to a cannula through which the surgical tool 1006 is slidably inserted.

Alternatively or additionally, the surgical tool 1006 mounted to the distal portion 606 of the remotely controllable manipulator 602 includes degrees of freedom, e.g., in addition to the degrees of freedom of the remotely controllable manipulator 602. Movement along the degrees of freedom of the distal end device is driven by, for example, motors of the remotely controllable manipulator 602. In the example shown in FIGS. 10A-10D, the surgical tool 1006 includes a rotational joint J8 proximally of the pivot point PP. The rotational joint J8 is, in some cases, disposed at a location of the access port. A distal wrist of the surgical tool 1006 allows pivotal motion of an end effector 1050 about the instrument wrist joint axes J4, J10. An angle α between end effector jaw elements can be controlled independently of the location and orientation of the end effector 1050.

In some implementations, to guide the insertion of the puncture device 106, the controller 702 provides operator guidance to move the puncture device along the insertion axis 508 of the puncture device 106. The controller 702 provides the operator guidance by, for example, controlling the indicator system 112 to generate the human-perceptible feedback. In some cases, the indicator system 112 includes the drive system 610, and the controller 702 operates the drive system 610 to generate the human perceptible feedback, such as, for example, tactile indication provided by operation of the motor or the brake of the drive system 610. In some cases, the controller 702 guides the insertion of the puncture device 106 by maintaining the angle 506 of the insertion axis 508 of the puncture device 106 within the predefined range as described herein. As a result, while the controller 702 maintains the angle 506 of the insertion axis 508, the operator guides insertion of the puncture device 106 along the insertion axis 508.

In some implementations, the controller 702 inhibits movement of the puncture device 106 by limiting a distance traveled by the puncture device 106. The controller 702, for instance, operates the drive system 610 to limit the puncture device 106 from travelling beyond a predefined distance corresponding to a predicted amount of travel from an outer surface of the tissue 108 to the cavity 110 or an inner surface of the tissue 108, from a location referenced to the patient anatomy, from an operator-settable location, etc. The predicted amount of travel may be predetermined or dynamically determined based on real-time information of the puncture operation. The controller 702 determines the distance traveled by the puncture device 106 based on the signal from the sensor system 704. In some implementations, the controller 702 inhibits movement of the puncture device 106 by limiting a velocity and/or an acceleration of the puncture device 106. The controller 702, for example, operates the drive system to prevent the puncture device 106 from having a velocity and/or an acceleration exceeding a predefined value.

In examples in which the remotely controllable manipulator 602 includes multiple joints to enable multiple degrees of freedom for the distal portion 606 of the remotely controllable manipulator 602, the controller 702 coordinates movements of the multiple joints to control movement about each degree of freedom for the distal portion 606. In some cases, the controller 702 operates the drive system 610 to enable movement in one degree of freedom while restricting movement in another degree of freedom. The drive system 610 is, for example, controlled such that the operator is able to freely move the puncture device 106 along the insertion axis 508 while being controlled such that rotation of the puncture device 106, e.g., relative to an axis perpendicular to the insertion axis 508, is restricted.

Example Sensor Systems and Related Methods

The examples of sensor systems described herein, e.g., the sensor system 104 and the sensor system 704, can be responsive to a variety of parameters or events associated with insertion of puncture devices. While the example sensor systems of FIGS. 11-17 are described as in communication with the controller 114, other controllers may be used instead. Other examples of controllers described herein (e.g., the controller 702 of the remotely controllable manipulator 602) can receive the signals generated by the sensor systems instead or in addition.

In certain examples, the sensor system includes a sensor responsive to a force. In the example depicted in FIG. 11, a surgical puncture device insertion system 1100 includes a force sensor 1104 to generate a signal in response to a force on the puncture device 106. The force sensor 1104, for example, generates the signal in response to force on the puncture device 106 when the puncture device 106 is being inserted through the tissue 108 and into the cavity 110. In some cases, the controller 114, based on the signal, determines that a value of the force, a profile of the force, and/or a rate of change of the force is outside of a predefined range.

In some implementations, the insertion system 1100 includes a handle 1106 to be grasped by an operator. To create the puncture through the tissue, the operator grasps the handle 1106 and manipulates the insertion system 1100, with the puncture device 106 mounted to the insertion system 1100, to insert the puncture device 106 through the tissue 108. In some cases, the force sensor 1104 is positioned between the puncture device 106 and the handle 1106.

In some cases, the force sensor 1104 is responsive to forces on the puncture device 106 along the insertion axis 508 of the puncture device 106. The controller 114 detects, for example, motion of the puncture device 106 between the different layers of the tissue 108 based on a signal generated by the force sensor 1104 in response to changes in axial force on the puncture device 106. Different layers of the tissue 108, for instance, each have a different stiffness that results in the force sensor measuring a different force for each layer.

In some examples, a change in the force is indicative of motion of the puncture device 106 from the tissue 108 into the cavity 110, e.g., the puncture device 106 being in the cavity 110. The change in the force corresponds to, for example, a sudden decrease in the measured force. The force while the distal portion 504 of the puncture device 106 is being inserted through the tissue 108 is, for example, greater than the force when the distal portion 504 of the puncture device 106 is positioned beyond the tissue 108 and within the cavity 110. The change in the force corresponds to, in some cases, a sudden increase in the measured force. In another example, the force while the distal portion 504 of the puncture device 106 is being inserted through a first layer of the tissue 108 is less than the force while the distal portion 504 of the puncture device 106 is being inserted through a second layer of the tissue 108.

Alternatively or additionally, the force sensor 1104 is responsive to forces perpendicular to the insertion axis 508 of the puncture device 106. The controller 114 determines, for example, an angle of the insertion axis 508 of the puncture device 106 relative to the tissue 108 based on the perpendicular forces.

While the sensor 1104 has been described as a force sensor, in some implementations, the sensor 1104 is alternatively or additionally a pressure sensor responsive to a pressure on the puncture device 106 or a torque sensor responsive to a torque on the puncture device 106. The controller 114 determines, for example, when the puncture device 106 moves between the different layers of tissue based on a signal generated by the sensor 1104 in response to changes in pressure or torque on the puncture device 106. In some cases, the force sensor 1104 is a six-axis inertial measurement unit (IMU) responsive to forces along and torques about three distinct axes.

In some implementations, the force sensor 1104 monitors the force and generates signals representing the monitored force. The controller 114 in turn determines when a signal from the force sensor is above a threshold value, for example, to guide insertion of the puncture device 106. In other implementations, the force sensor 1104 generates the signal in response to the force exceeding the threshold value without monitoring the force. The force sensor 1104 is, for example, a frangible connection that ruptures in response to a force exceeding the threshold value.

In certain examples, the sensor system includes a sensor responsive to a characteristic of an optical signal, e.g., an intensity, a wavelength, a frequency, a spectrum, etc., of the optical signal. In the example depicted in FIG. 12, a surgical puncture device insertion system 1200 includes an optical sensor 1202 that generates a signal in response to an optical signal.

The optical sensor 1202 is, for instance, a time-of-flight sensor. The characteristic of the optical signal corresponds to a characteristic of a reflection of an optical signal. The optical sensor 1202 includes an emitter 1204 to generate an optical signal and a photodetector 1206 to receive a reflection of the optical signal. The emitter 1204 directs the optical signal, for example, along the insertion axis 508 of the puncture device 106. The photodetector 1206 monitors reflected optical signals directed along the insertion axis 508 of the puncture device 106. The optical signal is, for example, a visible light beam or an infrared light beam. The controller 114 determines a distance between the distal portion 504 of the puncture device 106 and tissue distal to the distal portion 504 of the puncture device 106. The distance is determined, for example, based on an elapsed duration of time between emission of the optical signal by the emitter 1204 and receipt of the reflection of the optical signal by the photodetector 1206. The controller 114, based on the distance, detects motion of the puncture device 106 through the tissue 108, e.g., between different layers of tissue, and/or motion of the puncture device 106 into the cavity 110, e.g., from the tissue 108 into the cavity 110, the puncture device 106 being in the cavity 110.

In some implementations, the controller 114 determines a distance of patient tissue 108 from the optical sensor 1202 based on the optical signal. The controller 114, for example, determines that the distance of the patient tissue 108 is greater than a threshold distance. The controller 114 then, for example, operates the indicator system to produce the human-perceptible feedback in response to the distance being greater than the threshold distance.

The optical sensor 1202 alternatively or additionally includes an image capture device that generates a signal representing an image captured by optical sensor 1202. The optical sensor 1202 receives optical signals as the puncture device 106 is advanced through the tissue 108 and generates the signal representing the image based on the received optical signals. The controller 114, based on the image, determines a location of the puncture device 106 within the tissue 108 or within the cavity 110. The controller 114 thus is able to detect motion of the puncture device 106 within the tissue 108 and/or into the cavity 110 based on the image. In some implementations, the image capture device comprises an ultrasound device coupled to the puncture device 106 usable for monitoring a location of the puncture device 106 as the puncture device 106 is advanced through the tissue 108. The ultrasound device can be used to sense, for example, a distance traveled by the puncture device 106, a location of the puncture device 106 within the tissue 108, the presence or the absence of a cavity in the path of the puncture device 106, or a change in orientation of the puncture device 106.

In certain examples, the sensor system includes a sensor responsive to an electrical characteristic, e.g., associated with tissue of the patient. In the example shown in FIG. 13, a surgical puncture device insertion system 1300 includes a sensor system 1302 including an electrode 1304 on an outer surface of the puncture device 106.

In some implementations, as the puncture device 106 is inserted through the tissue 108, the sensor system 1302 generates a signal that varies depending on the layer of the tissue 108 proximate the electrode 1304. The tissue 108, for instance, includes several layers 1306*a*-1306*d*. Each layer of the tissue 108 has a unique electrical characteristic that enables the controller 114 to identify within which layer 1306*a*-1306*d* the electrode 1304 is positioned. The electrical characteristic associated with the tissue proximate the electrode 1304 includes, for example, an electrical capacitance, an electrical impedance, and/or an electrical inductance associated with the tissue 108. In this regard, a signal generated by the sensor system 1302 is indicative of, for example, a type of tissue proximate the electrode 1304.

In this regard, based on the signal from the sensor system 1302, the controller 114 is able to detect motion of the puncture device from a first layer of the tissue 108 to a second layer of the tissue 108. The controller 114, for example, detects a change in a value of the electrical characteristic and thereby detects motion from the first layer to the second layer of tissue 108. In some cases, the controller 114 is able to detect motion of the puncture device 106 from the tissue 108 into the cavity 110 due to a change in the value of the electrical characteristic. The sensor system 1302, for instance, detects bioelectrical impedance based on predefined impedances, e.g., an expected impedance of muscle tissue and/or an expected impedance of fat tissue. Muscle tissue, for example, has a lower impedance than fat tissue due to muscle tissue having a higher water concentration.

In some implementations, the sensor system 1302 includes multiple electrodes 1304*a*, 1304*b*, 1304*c*. Each electrode 1304*a*, 1304*b*, 1304*c* contacts a distinct portion of the tissue 108. In this regard, the sensor system 1302 is able to determine more precisely a location of the puncture device 106 within the tissue 108, e.g., the layer of tissue within which the distal portion of the puncture device 106 is located. In some implementations, the sensor system includes a matrix of electrodes such that the signals generated by the electrodes can be used to form an impedance map along the insertion axis of the puncture device 106. The impedance map can be used to indicate a relative location of anatomical structures, e.g., a relative location of different layers of patient tissue, a location of the cavity relative to the patient tissue.

In some implementations, the sensor system 1302 is configured to detect if patient tissue is proximate to the sensor system 1302, and not the separate layers of patient tissue 108. This sensor system 1302 then generates a signal indicative of the lack of proximate patient tissue 108 that occurs when the puncture device 106 is in the cavity 110. As a specific example, an implementation of the sensor system 1302 detects an electrical characteristic such as electrical impedance or electrical capacitance. The magnitude of the detected electrical characteristic is substantively different for the puncture device 106 being within the cavity 110 (without surrounding tissue 108) than for the puncture device 106 being within the tissue 108; for example, the electrical impedance may be much greater, and the electrical capacitance may be much lower, for the puncture device 106 being in the cavity 110 as compared to being in the tissue 108. This sensor system 1302 then generates a signal indicative of motion into the cavity in response to detecting a change in electrical characteristic beyond a threshold amount, and generates the signal indicating that the puncture device 106 has entered the cavity 110.

Alternatively or additionally, to detect an electrical characteristic of the tissue 108, the sensor system includes a cathode positioned on the puncture device 106 and an anode positioned on the tissue 108. A signal is generated at the cathode and transmitted through the tissue 108 to the anode. When the cavity 110 is breached by the puncture device 106, the signal may change resulting in detection by the puncture device 106.

In certain examples, the sensor system includes a sensor responsive to a material property associated with patient tissue. In the example shown in FIG. 14, a sensor system 1402 of a surgical puncture device insertion system 1400 includes a compressible device 1403 that, for instance, compresses an amount in proportion to a stiffness of tissue surrounding the compressible device 1403. The sensor system 1402 is positioned around the puncture device 106 such that the sensor system 1402 contacts a portion of the tissue 108 as the puncture device 106 is inserted through the tissue 108. The sensor system 1402 generates a signal indicative of an amount of compression of the compressible device 1403. The sensor system 1402, for example, includes capacitive devices 1404 coupled to the compressible device 1403. The capacitance of the capacitive devices 1404 varies, for example, relative to a material property of the portion of the tissue surrounding the sensor system 1402. The capacitance of the capacitive devices 1404 varies in proportion to, for instance, the stiffness of the surrounding tissue. The tissue 108, for example, includes a first layer and a second layer, the first layer having a greater stiffness than the second layer. In this regard, the sensor system 1402 experiences greater deformation due to contact with the first layer than due to contact with the second layer. The greater deformation causes the capacitance of the capacitive devices 1404 when the puncture device 106 is within the first layer of the tissue 108 to be greater than the capacitance of the capacitive devices 1404 when the puncture device 106 is within the second layer of the tissue 108. Based on the signal from the sensor system 1402, the controller 114 identifies the layer of the tissue 108. In some implementations, the sensor system 1402 includes a microelectromechanical (MEM) sensor, a flexible pressure sensor network, or other sensor to detect physical pressure or force.

In certain examples, the sensor system includes a sensor responsive to an audible signal. In the example shown in FIG. 15, a surgical puncture device insertion system 1500 includes an audio receiver 1502 to receive an audible signal generated as the puncture device 106 is inserted through the tissue 108. In some implementations, an audible signal is generated as the puncture device 106 moves from a first layer of tissue to a second layer of tissue. The insertion system 1500 includes, for instance, an audible signal generator 1504 that generates the audible signal in response to motion of the puncture device 106 from the first layer of the tissue 108 to the second layer of the tissue 108. In another example, the audible signal generator 1504 generates the audible signal in response to motion of the puncture device 106 from the tissue 108 into the cavity 110.

In some implementations, the audible signal generator 1504 includes a resilient member 1506, e.g., a compression spring, and an obturator 1508. The resilient member 1506 biases the obturator 1508 distally. The resilient member 1506, for example, is positioned such that a proximal end of the resilient member 1506 bears against a housing 1510 of the insertion system 1500 and a distal end of the resilient member 1506 bears against the obturator 1508. In some implementations, the housing 1510 corresponds to a housing of the puncture device 106, for example, a hub on a proximal portion of the puncture device 106.

During insertion of the puncture device 106 into the tissue 108, the obturator 1508 is pushed against the tissue 108 such that the obturator 1508 is moved proximally, thereby compressing the resilient member 1506. A distal portion 1512 of the obturator 1508, for example, contacts the tissue 108 while the distal portion 504 of the puncture device 106 is within the tissue 108. When the puncture device 106 is inserted through the tissue 108 such that the distal portion 504 of the puncture device 106 extends into the cavity 110, the obturator 1508 is movable distally. In this regard, the resilient member 1506 is released, causing the obturator 1508 to move in the distal direction relative to the housing 1510. A distal facing surface 1514 of the obturator 1508 impacts the housing 1510, thereby generating an audible signal. The audio receiver 1502 is positioned to receive the audible signal. The audio receiver 1502, for example, generates a signal in response to the audible signal. The controller 114, based on the signal from the audio receiver 1502, detects motion of the puncture device 106 from the tissue 108 into the cavity 110.

In certain examples, the sensor system 104 includes a sensor responsive to a pressure, e.g., a fluid pressure. In the example depicted in FIG. 16, a surgical puncture system 1600 includes a sensor system 1602 including a pressure sensor 1604. The pressure sensor 1604 is responsive to a pressure proximate the distal portion 504 of the puncture device 106. The surgical puncture system 1600 includes an insufflator 1606 that ejects fluid, e.g., a gas or a liquid, into a region surrounding the distal portion 504 of the puncture device 106. If gas, the fluid is, for example, $CO_2$. If liquid, the fluid is, for example, saline.

In some examples, the puncture device 106 is hollow, and a hub 1608 on the puncture device 106 connects the insufflator 1606 such that air ejected from the insufflator 1606 can be delivered through the puncture device 106 to the distal portion 504 of the puncture device 106. The pressure sensor 1604 is positioned to be in fluid communication with the insufflator and the distal portion 504 of the puncture device 106. In this regard, the pressure sensor 1604 generates a signal in response to fluid pressure at the distal portion 504 of the puncture device 106.

The insufflator 1606, for example, delivers the fluid to the region surrounding the distal portion 504 of the puncture device 106, and the pressure sensor 1604 detects the pressure caused by the delivered fluid in the region. The fluid pressure measured by the pressure sensor 1604 when the distal portion 504 of the puncture device 106 is within the tissue 108 is greater than the fluid pressure measured by the pressure sensor 1604 when the distal portion 504 of the puncture device 106 is within the cavity 110. In this regard, in response to a signal from the pressure sensor 1604, the controller 114 is able to detect motion of the puncture device 106 from the tissue 108 into the cavity 110.

In some implementations, the controller 114 operates the insufflator 1606 such that the flow rate of the fluid delivered by the insufflator 1606 is constant while the controller 114 detects the distal portion 504 is within the tissue 108. When the controller 114 detects motion of the insufflator 1606 from the tissue 108 into the cavity 110, the controller 114 increases the flow rate of the fluid. The controller 114, for instance, operates the insufflator 1606 to eject fluid at a first flow rate in response to the pressure sensor 1604 generating a first signal indicating that the distal portion 504 of the puncture device 106 is in the tissue 108. The controller 114 operates the insufflator 1606 to eject fluid at a second flow rate, greater than the first flow rate, in response to the pressure sensor 1604 generating a second signal indicating that the distal portion 504 of the puncture device 106 is in the cavity 110.

In some implementations, the insufflator 1606 dispenses fluid at a flow rate of less than 3 liters per minute during the initial insertion of the puncture device 106, e.g., as the puncture device 106 is initially introduced into the tissue of the patient. After the puncture device 106 is inserted into the cavity, in some cases, the flow rate is increased to a greater flow rate, e.g., 4 to 8 liters per minute. In some cases, if the signal generated by the pressure sensor 1604 indicates a pressure greater than a threshold pressure, e.g., that is between 8 mmHg and 15 mmHg, that is about 10 mmHg, the controller 114 determines that the puncture device 106 has not penetrated into the cavity 110. In some cases, if the signal generated by the pressure sensor 1604 indicates a pressure less than another threshold pressure, e.g., between 1 mmHg and 3 mmHg, the controller 114 determines the puncture device 106 has penetrated into the cavity 110 and then increases the flow rate of the insufflator 1606.

Example Stabilizing Systems and Related Methods

In some implementations, when the puncture device 106 is inserted into the tissue 108, a region surrounding the tissue 108 is stabilized. In the example shown in FIG. 17, a surgical puncture device insertion system 1700 includes a stabilizing device 1702. The puncture device insertion system 1700 can include a sensor system as described herein. The puncture device 106 is integral to the puncture device insertion system 1700 or is mounted prior to insertion of the puncture device 106 into the tissue 108.

The stabilizing device 1702, for example, applies a force to a region 1704 of the tissue 108 including an insertion site 1706 through which the puncture device 106 is to be inserted. The stabilizing device 1702 includes, in some cases, a grasping member 1708 to apply the force to the region 1704 of the tissue 108.

The grasping member 1708 is, for example, actuated to grasp the tissue 108 in the region 1704. A drive system 1709, in some cases, operates the grasping member 1708 to grasp the tissue 108. Alternatively, a human operator manually manipulates the grasping member 1708 to grasp the tissue 108. In some implementations, the drive system 1709 is part of a remotely controllable manipulator, e.g., the remotely controllable manipulator 602. The grasping member 1708 is manipulated by the remotely controllable manipulator to apply the force to the region 1704. The grasping member 1708, for instance, is able to be articulated to apply the grasping force on the tissue 108. In some implementations, the grasping member 1708 includes forceps manipulated to provide a traction force on the tissue 108. In some cases, a sensor generates a signal indicative of a position of the grasping member 1708, e.g., the sensor is a force or pressure sensor. The signal, for example, is indicative of an amount of displacement or the tissue caused by the grasping member 1708.

Alternatively or additionally, the stabilizing device 1702 includes a vacuum inlet 1710 to be connected to a suction device 1712 Sealing members 1714 of the stabilizing device 1702 contact the tissue 108 to create sealing contact between the stabilizing device 1702 and the tissue 108. The suction device 1712 generates suction to apply traction to the region 1704 of the tissue 108.

In some implementations, the stabilizing device 1702 includes an alignment member 1716 positioned to inhibit lateral movement of the puncture device 106. The alignment member 1716 inhibits movement of the puncture device 106 such that an angle of the insertion axis 508 of the puncture device 106 relative to the outer surface of the tissue 108 is within a predefined angle. In some implementations, the alignment member 1716 inhibits movement such that the insertion axis 508 is substantially perpendicular to the outer surface of the tissue 108. The alignment member 1716 supports a proximal portion of the puncture device 106, and another alignment member 1718 support a distal portion of the puncture device 106. The alignment members 1716, 1718 cooperate to inhibit the lateral movement of the puncture device 106. In some implementations, the predefined angle is adjustable. The puncture device 106 is mounted to the stabilizing device 1702, and the stabilizing device 1702 is rotatable about a joint 1722. In some cases, the alignment members 1716 and 1718 are part of the instrument holder 1020 of the remotely controllable manipulator 602. The remotely controllable manipulator 602, for example, guides and inserts the puncture device 106 while maintaining a stabilizing force on the tissue, using the stabilizing device 1702, within a predefined range.

Alternative Implementations

A number of implementations have been described. Nevertheless, it will be understood that various modifications may be made.

The sensor systems described herein can be combined in a surgical puncture device insertion system to provide orthogonal processes of detecting motion of the puncture device between layers of tissue or from the tissue into the cavity. The surgical puncture device insertion system includes a sensor system including, for example, two or more of an optical sensor, a pressure sensor, an audio receiver, or other sensors described herein. In some cases, one sensor of the sensor system generates the signal for detecting motion of the puncture device from one layer of tissue to another layer of tissue, and the other sensor of the sensor system generates the signal for detection motion of the puncture device from the tissue into the cavity. Furthermore, in some cases, one sensor monitors a parameter associated with insertion of the puncture device, while the other sensor generates a signal in response to an event associated with insertion of the puncture device.

In some implementations, the puncture is made through an incision that does not pierce into the cavity. An obturator-cannula assembly is then used to punch through the tissue such that the puncture extends through the tissue to the cavity. After insertion, the obturator can be removed from the cannula to provide the access port to the cavity. In this regard, the systems herein can be used to provide human-perceptible feedback to guide movement of the obturator used to punch through the tissue. The sensor systems, for example, detect insertion of the obturator as the obturator is inserted through the incision. The sensor systems additionally detect insertion of the obturator into the cavity as the obturator punches through the tissue. In particular, the sensor systems detect when the obturator is positioned in the cavity, using the processes described herein.

In some implementations, a first puncture is created and a first surgical tool is inserted through the first puncture to perform a surgical operation. In some cases, a first puncture is created and not used for inserting surgical tools, and a second puncture is created for inserting one or more surgical tools. In some cases, multiple surgical tools are inserted through the first puncture to perform the surgical operation. Alternatively, a single surgical tool is inserted through the first puncture, and a second puncture is created for inserting a second surgical tool. During the surgical operation, one or more surgical tools may be removed and reinserted through respective puncture(s), or replaced with other surgical tool(s) through respective puncture(s).

In some cases, the sensor system includes an accelerometer or an inertial measurement unit to generate a signal indicative of motion of the puncture device 106. For instance, if the insertion system includes a module including the sensor system, the accelerometer and/or the inertial measurement unit generate signals that indicate how quickly the operator is inserting the puncture device through tissue of the patient.

In some implementations, the sensor system includes a receiver connected to the controller 114. The sensor system further includes another sensor, for example, one of the sensors described herein. In this regard, the controller 114, in some cases, is wirelessly connected to the other sensor through the receiver. The other sensor, for example, senses the motion of the puncture device 106 through the tissue and/or into the cavity and generates the signal indicative of the motion, the receiver receives data from the other sensor, e.g., receives a wireless signal representing the generated signal indicative of motion and then transmits information representing the generated signal to the controller 114.

While the human-perceptible feedback is described as being generated in response to motion of the puncture device 106 through the tissue 108, alternatively or additionally, a human-perceptible feedback is produced when the puncture device 106 is to be initially inserted into the tissue 108. The controller 114 detects, for instance, when the insertion axis 508 is aligned with a target insertion site. The sensor system 104 includes a sensor that generates a signal indicative of a position and/or orientation of the insertion axis 508 relative to the insertion site. In this regard, the controller 114 produces the human-perceptible feedback to indicate that the insertion axis 508 is aligned with the insertion site.

The layers of the tissue 108 described herein are of different types. The types of the tissue 108 include, for instance, skin, fat, muscle, peritoneum, etc. Each layer of tissue has distinct properties. For example, the stiffness of each type of layer is distinct from the stiffnesses of other layers. The sensor system, in this regard, can generate a signal responsive to the stiffness of the tissue. Other properties, such as electrical characteristics and visual identifiers like color and texture, can vary between different types of layers. In some implementations, the controller 114 accesses memory that stores predefined information associated with each type of layer of the tissue to be punctured. Based on a signal from the sensor system and the predefined information, the controller 114 determines which layer of tissue the puncture device 106 is within. The layers of tissue vary in, for example, stiffness, fluid content, conductivity, compliance, etc. The memory stored, for example, predefined information indicative of values of these characteristics for different types of tissue. The sensor system, for example, generates a signal representing a value of characteristic of a layer of tissue proximate the puncture device 106 such that the controller 114 can determine the type of tissue proximate the puncture device 106 based on the sensor signal and the stored predefined values.

In some implementations, values for thresholds, ranges, and other predefined parameters described herein are altered with each operation of the insertion system. The controller 114, for instance, sets a predefined threshold and/or a predefined range based on previous values measured during an insertion operation for a puncture device.

Figure 18:
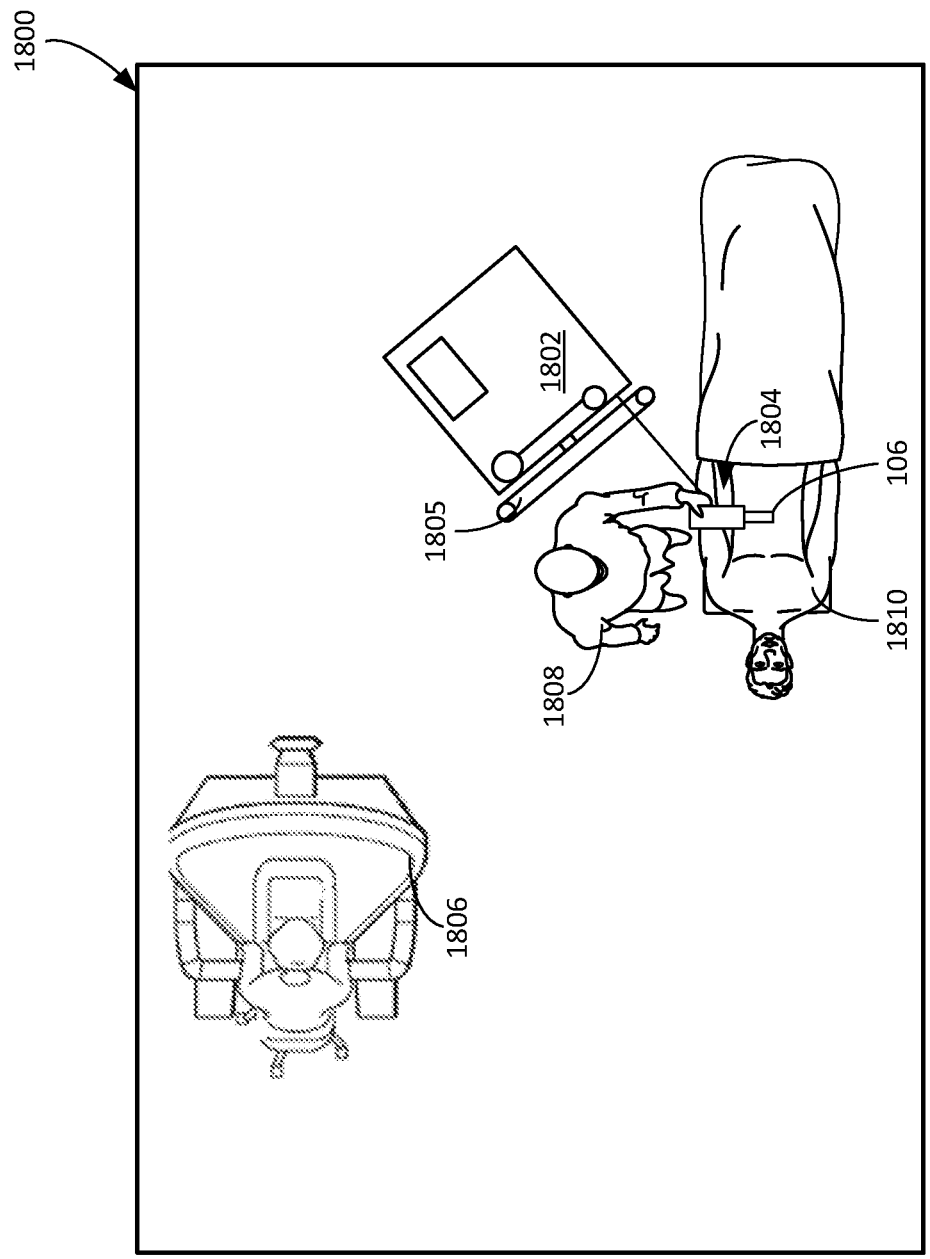
FIG. 18 is a top view of a surgical system including an electronic cart.

As described herein, in some cases, the signal provided by the sensor system can be provided by a system separate from the remotely controllable manipulator. In some implementations, the insertion system including the sensor system to provide the signal is a standalone unit, e.g., independent of a device to be used when the surgical tool is inserted to perform the surgical operation. In some implementations, the insertion system is connected to the remotely controllable manipulator or other element of the surgical system, e.g., a surgeon's console, a vision cart, an electronics cart etc. Referring to FIG. 18, in some implementations, a surgical system 1800 includes an electronics cart 1802, e.g., a vision cart, to be connected to a surgical puncture device insertion system 1804. A controller of the electronics cart 1802 corresponds to the controller 114 to operate the insertion system 1804. The electronics cart 1802, for example, is connected with an imaging device that generates the images of the surgical site. In some implementations, the electronics cart 1802 further includes a display 1805 to present the images to a human operator 1808. The remotely controllable manipulator 602, for example, includes the imaging device connected to the electronics cart 1802. The imaging device includes, for example, illumination equipment (e.g., a Xenon lamp) that provides illumination for imaging the surgical site. The imaging device, for example, captures the images and then transmits the images to the electronics cart 1802 for processing. The electronics cart 1802 transmits the images to the surgeon's console 1806 so that the processed images can be presented to the surgeon. The electronics cart 1802 can include optional auxiliary surgical equipment, such as electrosurgical units, insufflators, suction irrigation instruments, or third-party cautery equipment. Furthermore, as shown in FIG. 18, in some cases, the operator 1808 manually manipulates the puncture device 106 to cause the puncture device 106 to be inserted into a patient 1810.

While the auxiliary device 711 has been described as a stabilizing device and/or an insufflator, in some implementations, the auxiliary device includes a device to sense characteristics of the patient. The auxiliary device includes, for instance, device measure pulse, blood pressure, or other information related to vasculature of the patient. The auxiliary device generates a signal, for instance, to detect a vasculature complexity, e.g., iatrogenic damage to the vasculature. In some implementations, the auxiliary device includes a sensor to measure ventilation pressure and/or saturation of oxygen from a ventilator. The auxiliary device includes, for example, a pulse oximetry device to measure oxygen saturation. In some implementation, the auxiliary device includes a sensor to measure a posture of the patient, e.g., to determine whether the patient is supine. The posture of the patient includes, for example, a position or an orientation of the patient. The sensor is, for example, a position sensor, an accelerometer, or other sensor that generates a signal indicative of the position of the patient. Alternatively or additionally, the auxiliary device includes a sensor to generate a signal indicative of an angle, a tile, and/or a position of a table supporting the patient. The signal can indicate a position or orientation of the patient. In some implementation, the auxiliary device includes a sensor attached to, for example, the operating table, that would measure the weight of the patient and/or that would measure the force transferred through the table from the puncture device as it is inserted through the patient. In some cases, if the sensor measures the weight of the patient, the auxiliary device is used to verify patient information, e.g., a BMI of the patient. In some cases, if the sensor measures the force of the puncture device as it is transferred through the table, the signal generated by the sensor is used by the controller to provide the human-perceptible feedback, e.g., to indicate when the force is too high.

In some implementation, the auxiliary device corresponds to a device that provides information as the puncture device is inserted through the patient. The auxiliary device, for example, includes an imaging device, such as a computed tomography (CT) scanner, a magnetic resonance imaging (MRI) device, a fluoroscopy imaging device, an ultrasound device, or other imaging device that generates images of the patient tissue and/or cavity. In some cases, the auxiliary device includes an ultrasound device to identify whether patient anatomy near the site of insertion is an adhesion to be avoided by the puncture device.

While the puncture device insertion systems are described as being usable with surgical tools and as being usable for surgical operations, in some implementations, the puncture device insertion systems are usable with other medical tools and usable for other medical operations. In some implementations, rather than corresponding to a surgical tool, the medical tool corresponds to a needle. For example, the puncture device 106 can be used to position a needle for administering epidural anesthesia. The cavity 110 corresponds to an epidural space of the patient. The puncture device 106 is inserted into patient tissue to access the epidural space, and the needle is inserted into the epidural space to administer the anesthesia. In some implementations, the puncture device 106 is used to place a needle into a vein for blood withdrawal from a patient or for fluid delivery to a patient. The cavity 110 corresponds to a vein of the patient. The puncture device 106 is inserted into the patient tissue, and the needle is inserted into the puncture device 106 and then into the vein to create fluid communication with the vein.

Figure 19:
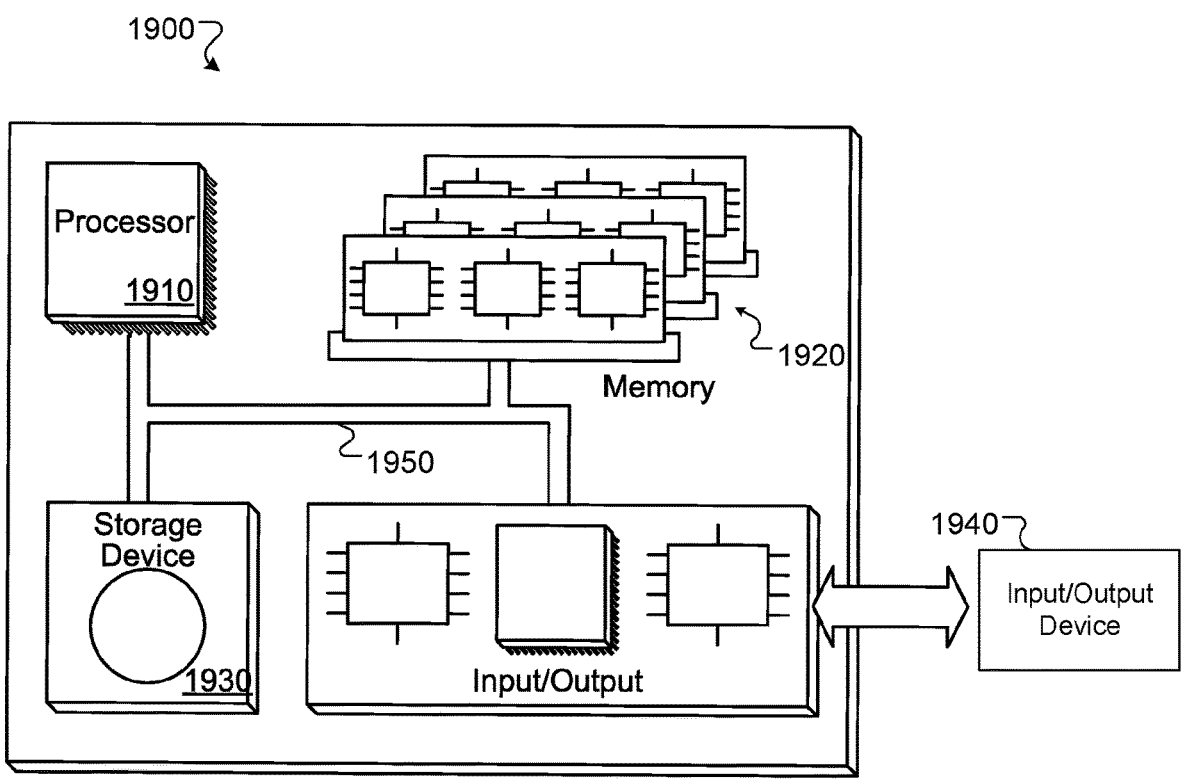
FIG. 19 is a schematic diagram of a computer system.

Controllers and any associated components described herein can be part of a computing system that facilitates control of the insertion systems according to processes and methods described herein. FIG. 19 is a schematic diagram of an example of a computer system 1900 that can be used to implement a controller, e.g., the controller 114, described in association with any of the computer-implemented methods described herein. The system 1900 includes components such as a processor 1910, a memory 1920, a storage device 1930, and an input/output device 1940. Each of the components 1910, 1920, 1930, and 1940 are interconnected using a system bus 1950. The processor 1910 is capable of processing instructions for execution within the system 1900. In some examples, the processor 1910 is a single-threaded processor, while in some cases, the processor 1910 is a multi-threaded processor. The processor 1910 is capable of processing instructions stored in the memory 1920 or on the storage device 1930 to display graphical information for a user interface on the input/output device 1940.

Memory storage for the system 1900 can include the memory 1920 as well as the storage device 1930. The memory 1920 stores information within the system 1900. The information can be used by the processor 1910 in performing processes and methods described herein. In some examples, the memory 1920 is a computer-readable storage medium. The memory 1920 can include volatile memory and/or non-volatile memory. The storage device 1930 is capable of providing mass storage for the system 1900. In general, the storage device 1930 can include any non-transitory tangible media configured to store computer readable instructions. Optionally, the storage device 1930 is a computer-readable medium. Alternatively, the storage device 1930 may be a floppy disk device, a hard disk device, an optical disk device, or a tape device.

The system 1900 includes the input/output device 1940. The input/output device 1940 provides input/output operations for the system 1900. In some examples, the input/output device 1940 includes a keyboard and/or pointing device. In some cases, the input/output device 1940 includes a display unit for displaying graphical user interfaces.

The features of the methods and systems described in this application can be implemented in digital electronic circuitry, or in computer hardware, firmware, or in combinations of them. The features can be implemented in a computer program product tangibly stored in an information carrier. The information carrier can be, for example, a machine-readable storage device, for execution by a programmable processor. Operations can be performed by a programmable processor executing a program of instructions to perform the functions described herein by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages. The computer program can be deployed in any form, including as a stand-alone program or as a module, component, subroutine, or other unit suitable for use in a computing environment.

Generally, a computer will also include, or be operatively coupled to communicate with, one or more mass storage devices for storing data files. Such devices can include magnetic disks, such as internal hard disks and removable disks, magneto-optical disks, and optical disks. Storage devices suitable for storing the computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

Alternatively, the computer can have no keyboard, mouse, or monitor attached and can be controlled remotely by another computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

The processor 1910 carries out instructions related to a computer program. The processor 1910 can include hardware such as logic gates, adders, multipliers and counters. The processor 1910 can further include a separate arithmetic logic unit (ALU) that performs arithmetic and logical operations.

Accordingly, other implementations are within the scope of the claims.

What is claimed is:

1. A medical puncture system comprising:
    a controllable manipulator comprising:
        a holder configured to support a puncture device and configured to support a medical tool, the puncture device configured to create a puncture through patient tissue and into an internal patient cavity to enable an end effector of the medical tool to be inserted through the puncture into the cavity, wherein the controllable manipulator comprises one or more joints and a sensor configured to generate signals indicative of a parameter associated with a joint of the one or more joints;
    a drive system configured to drive the one or more joints of the controllable manipulator to control motion of the puncture device when the puncture device is supported by the controllable manipulator, and to control motion of the medical tool when the medical tool is supported by the controllable manipulator; and
    a controller operably coupled to the sensor and the drive system, the controller configured to:
        receive information indicative of a keepout volume,
        when the puncture device is supported by the holder of the controllable manipulator, operate the drive system, based on at least one signal generated by the sensor as the puncture device is moved through the patient tissue into the cavity and the information indicative of the keepout volume, to cause the controllable manipulator to guide creation of the puncture by the puncture device and to cause the controllable manipulator to inhibit movement of the puncture device into the keepout volume, the at least one signal being indicative of motion of the puncture device from a first layer of the patient tissue to a second layer of the patient tissue or indicative of the puncture device being in the cavity, and
        when the medical tool is supported by the holder of the controllable manipulator and the end effector is inserted through the puncture into the cavity, operate the drive system to cause the controllable manipulator to control movement of the end effector in the cavity.

2. The medical puncture system of claim 1, wherein the medical puncture system further comprises an indicator system, and wherein the indicator system is operable by the controller to produce human-perceptible feedback based on the at least one signal in combination with patient information.

3. The medical puncture system of claim 2, wherein the patient information is indicative of a location of an insertion site for the puncture.

4. The medical puncture system of claim 2, wherein the patient information is indicative of a physical characteristic of a patient.

5. The medical puncture system of claim 4, wherein the physical characteristic comprises a size of the patient or a thickness of the patient tissue.

6. The medical puncture system of claim 1, wherein the information indicative of the keepout volume is indicative of one or more anatomical features to be avoided by the puncture device.

7. The medical puncture system of claim 1, wherein the keepout volume comprises an operator-selected keepout volume.

8. The medical puncture system of claim 1, wherein the parameter associated with the joint comprises at least one parameter selected from the group consisting of: a force applied to the joint, a torque applied to the joint, a motion of the joint, and an electrical current or voltage associated with the joint.

9. The medical puncture system of claim 1, wherein the sensor comprises at least one sensor selected from the group consisting of: an encoder, an accelerometer, a force sensor, and a torque sensor.

10. The medical puncture system of claim 1, wherein the at least one signal comprises:
    a first signal indicative of the motion of the puncture device from the first layer of the patient tissue to the second layer of the patient tissue; and
    a second signal indicative of the puncture device being in the cavity.

11. The medical puncture system of claim 1, wherein the at least one signal being indicative of the motion of the puncture device from the first layer of the patient tissue to the second layer of the patient tissue or indicative of the puncture device being in the cavity is indicative of a change in the parameter associated with the joint.

12. The medical puncture system of claim 1, wherein the controller is configured to operate the drive system based on the at least one signal to cause the controllable manipulator to guide the creation of the puncture by:
    operating the drive system to inhibit movement of the puncture device in response to the at least one signal.

13. The medical puncture system of claim 12, wherein operating the drive system to inhibit the movement of the puncture device comprises:
    inhibiting a range of motion of the puncture device.

14. The medical puncture system of claim 13, wherein inhibiting the range of motion of the puncture device comprises:
    inhibiting translational motion of the puncture device to within a distance of an initial position of the puncture device.

15. The medical puncture system of claim 13, wherein inhibiting the range of motion of the puncture device comprises:

inhibiting movement of the puncture device such that an angle of an insertion axis of the puncture device relative to the patient tissue is within a predefined range.

16. The medical puncture system of claim 1, wherein the at least one signal is indicative of motion of the puncture device from the patient tissue into the cavity.

17. The medical puncture system of claim 1, wherein the sensor is a first sensor, and the medical puncture system further comprises a second sensor configured to generate a signal indicative of motion of the puncture device through the patient tissue or into the cavity, the second sensor comprising at least one sensor selected from the group consisting of:
  a compressible device configured to compress relative to a stiffness of the patient tissue surrounding the compressible device, and the signal is indicative of the stiffness of the patient tissue; or
  an optical sensor configured to emit light and detect a reflection of the light to generate the signal; or
  an audible signal sensor configured to generate the signal in response to an audible signal indicative of the puncture device moving through the patient tissue or moving into the cavity; or
  a force sensor configured to generate the signal in response to a force on the puncture device; or
  an electrical characteristic sensor configured to detect at least one electrical characteristic selected from the group consisting of: an electrical capacitance associated with the patient tissue, an electrical impedance associated with the patient tissue, an electrical inductance associated with the patient tissue; or
  a pressure sensor to generate the signal in response to a pressure proximate a distal portion of the puncture device.

18. The medical puncture system of claim 1, wherein the holder is positioned on a distal portion of the controllable manipulator.

19. The medical puncture system of claim 1, wherein the controller is configured to operate the drive system to cause the controllable manipulator to control movement of the end effector in the cavity when the medical tool is supported by the holder of the controllable manipulator and the end effector is inserted through the puncture into the cavity by:
  operating the drive system to cause the controllable manipulator to control movement of the end effector in the cavity when the end effector is inserted through a port device in the puncture forming an access port to the cavity, wherein the puncture device comprises the port device or the port device is inserted into the puncture after the puncture device creates the puncture.

20. The medical puncture system of claim 1, wherein the at least one signal is indicative of motion of the puncture device from the first layer of the patient tissue to the second layer of the patient tissue.

21. A puncture device insertion system comprising:
  a controllable manipulator comprising:
    a holder configured to support a puncture device and configured to support a medical tool, the puncture device configured to create a puncture through patient tissue into an internal patient cavity, thereby enabling the medical tool to be inserted through the puncture into the cavity, wherein the controllable manipulator comprises one or more joints and a sensor configured to generate signals indicative of a parameter associated with a joint of the one or more joints;
    a drive system configured to drive the one or more joints of the controllable manipulator to control motion of the puncture device when the puncture device is supported by the controllable manipulator, and to control motion of the medical tool when the medical tool is supported by the controllable manipulator; and
  a controller operably coupled to the sensor and the drive system, the controller configured to:
    receive information indicative of a keepout volume,
    when the puncture device is supported by the holder of the controllable manipulator, operate the drive system, based on at least one signal generated by the sensor as the puncture device is moved through the patient tissue into the cavity and the information indicative of the keepout volume, to cause the controllable manipulator to guide creation of the puncture by the puncture device and to cause the controllable manipulator to inhibit movement of the puncture device into the keepout volume, the at least one signal being indicative of motion of the puncture device from a first layer of the patient tissue to a second layer of the patient tissue or indicative of the puncture device being in the cavity, and
    when the medical tool is supported by the holder of the controllable manipulator, operate the drive system to cause the controllable manipulator to control movement of the medical tool.

22. The puncture device insertion system of claim 21, wherein the controller is configured to operate the drive system based on the at least one signal to cause the controllable manipulator to guide the creation of the puncture by:
  operating the drive system to inhibit movement of the puncture device in response to the at least one signal.

23. The puncture device insertion system of claim 22, wherein operating the drive system to inhibit the movement of the puncture device comprises:
  inhibiting a range of motion of the puncture device.

24. The puncture device insertion system of claim 23, wherein inhibiting the range of motion of the puncture device comprises:
  inhibiting translational motion of the puncture device to within a distance of an initial position of the puncture device.

25. The puncture device insertion system of claim 23, wherein inhibiting the range of motion of the puncture device comprises:
  inhibiting movement of the puncture device such that an angle of an insertion axis of the puncture device relative to the patient tissue is within a predefined range.

26. The puncture device insertion system of claim 21, wherein the controller is configured to operate the drive system based on the at least one signal to cause the controllable manipulator to guide the creation of the puncture by:
  receiving patient information, the patient information comprising information selected from the group consisting of: a location of an insertion site for the puncture, a physical characteristic of a patient, and data representing an image of the patient tissue and the cavity; and
  adjusting a guidance provided for the creation of the puncture based on the patient information.

27. A method of operating a controllable manipulator, the method comprising:

receiving information indicative of a keepout volume;

detecting, based on at least one signal generated by a sensor of the controllable manipulator and indicative of a parameter associated with a joint of one or more joints of the controllable manipulator, motion of a puncture device supported by a holder of the controllable manipulator through patient tissue into an internal patient cavity or from a first layer of the patient tissue to a second layer of the patient tissue and causing the controllable manipulator, based on the detected motion and the information indicative of the keepout volume, to guide insertion of the puncture device through the patient tissue into the cavity and to inhibit movement of the puncture device into the keepout volume; and causing the controllable manipulator to control a medical tool supported by the holder of the controllable manipulator.

28. The method of claim 27, wherein causing the controllable manipulator to guide insertion of the puncture device comprises:

inhibiting movement of the puncture device in response to detecting the motion of the puncture device through the patient tissue into the cavity.

29. The method of claim 27, wherein causing the controllable manipulator to guide insertion of the puncture device comprise:

inhibiting a range of motion of the puncture device.

30. The method of claim 27, wherein causing the controllable manipulator to guide insertion of the puncture device comprises:

inhibiting translational motion of the puncture device to within a distance of an initial position of the puncture device; or inhibiting movement of the puncture device such that an angle of an insertion axis of the puncture device relative to the patient tissue is within a predefined range.

* * * * *